United States Patent
Martin et al.

(10) Patent No.: US 9,913,746 B2
(45) Date of Patent: Mar. 13, 2018

(54) CERVICAL COLLAR WITH HEIGHT ADJUSTMENT MECHANISM

(71) Applicant: Otto Bock HealthCare LP, Minneapolis, MN (US)

(72) Inventors: Michael L. Martin, West Jordan, UT (US); Kwok Tim Ng, Fanling (HK)

(73) Assignee: OTTO BOCK HEALTHCARE LP, Minneapolis, MN (US)

( * ) Notice: Subject to any disclaimer, the term of this patent is extended or adjusted under 35 U.S.C. 154(b) by 462 days.

(21) Appl. No.: 14/328,413

(22) Filed: Jul. 10, 2014

(65) Prior Publication Data

US 2016/0008158 A1    Jan. 14, 2016

(51) Int. Cl.
*A61F 5/00* (2006.01)
*A61F 5/055* (2006.01)

(52) U.S. Cl.
CPC ...... *A61F 5/055* (2013.01); *A61F 2250/0004* (2013.01)

(58) Field of Classification Search
CPC .............. A61F 2250/0004; A61F 5/055; A61F 2250/0003
USPC ...................................... 602/17, 18
See application file for complete search history.

(56) References Cited

U.S. PATENT DOCUMENTS

| | | | |
|---|---|---|---|
| 2,801,630 A * | 8/1957 | Moore | A61F 5/055 128/DIG. 23 |
| D188,302 S * | 6/1960 | Monfardini | 602/18 |
| 9,421,119 B2 * | 8/2016 | Suarez | A61F 5/055 |
| 2007/0270728 A1 * | 11/2007 | Chao | A61F 5/055 602/18 |
| 2009/0198163 A1 * | 8/2009 | Senyei | A61F 5/048 602/18 |
| 2011/0066094 A1 * | 3/2011 | Thorgilsdottir | A61F 5/055 602/6 |
| 2012/0130295 A1 * | 5/2012 | Haider | A61F 5/055 602/18 |
| 2013/0310722 A1 * | 11/2013 | Thorsteinsdottir | A61F 5/055 602/18 |
| 2014/0012172 A1 * | 1/2014 | Calco | A61F 5/055 602/18 |
| 2014/0107551 A1 * | 4/2014 | Modglin | A61F 5/055 602/18 |
| 2015/0190266 A1 * | 7/2015 | Hollern | A61F 5/055 602/18 |
| 2016/0058601 A1 * | 3/2016 | Garth | A61F 5/055 602/18 |

FOREIGN PATENT DOCUMENTS

JP     2012125525     7/2012

OTHER PUBLICATIONS

Partial International Search for International Patent Application No. PCT/US2015/037223, dated Sep. 24, 2015.

* cited by examiner

Primary Examiner — Kim M Lewis
(74) Attorney, Agent, or Firm — Holland & Hart

(57) ABSTRACT

A cervical collar provides height adjustment using a locking member disposed on a height adjustment member extending through a height adjustment aperture. As the locking member is moved between locked and unlocked positions, ridges on a main collar body and on a chin support member may be interlocked or allowed to slide over each other from one desired position to another, thereby providing a height adjustment mechanism for the cervical collar.

13 Claims, 18 Drawing Sheets

CERVICAL COLLAR WITH HEIGHT ADJUSTMENT MECHANISM

BACKGROUND

The following relates generally to orthopedic neck braces and specifically to cervical collars with height adjustment features.

The human spine has seven vertebrae in the neck that are referred to as the cervical vertebrae. When a person suffers a traumatic head or neck injury, fractures of the cervical vertebrae, strains, sprains, and whiplash symptoms may injure a person's spinal cord and other sensitive structures in the neck. Cervical collars are a type of neck brace used to support and immobilize a patient's neck, to help realign the spinal cord, and to relieve pain. They do so by limiting the head from tilting through use of bracing supports positioned around the patient's neck and under the patient's chin. Cervical collars may be rigid, padded braces or relatively soft and flexible. Typically, more rigid braces are used when there is an elevated risk of damage to the spinal cord, and softer braces are used in applications such as therapeutic recovery, where the patient's neck is stronger or the vertebrae and muscles have mostly healed.

A paramount concern in the use of cervical collars is the comfort of the patient. A cervical collar provides sustained support to the appropriate sides of the head and neck while minimizing the hindrance to the patient's mobility and ability to perform common tasks such as speaking or eating. Since patients come in all shapes and sizes, it is difficult for collars to do both jobs effectively. Too often, a cervical collar that is comfortable is not effective in medical treatment or a collar that provides proper support is restrictive and claustrophobic for the patient.

Some cervical collars have been developed with mechanisms that allow the patient and medical personnel to adjust the shape and support of the collar in an effort to provide a custom fit for the wearer. While these apparatuses succeed in addressing some of the issues faced by patients and medical personnel, they are frequently expensive to produce and subsequently expensive for a patient in need. Additionally, the adjustment mechanisms can be complex and unreliable, leading to confusion of the patient in the use of the device or unwanted and undesirable movement of the brace and the patient's neck.

SUMMARY

According to at least one embodiment, a height-adjustable cervical collar is provided, comprising a main collar body having a collar front portion and collar side portions. The collar front portion may be configured to be positioned anterior to a neck and upper chest area of a wearer, and the collar side portions may be configured to be positioned to the lateral sides of the neck of the wearer. At least one of the collar side portions may comprise at least one height adjustment aperture. The collar may also comprise a chin support member coupled to the main collar body, wherein the chin support member may have a chin front portion and chin side portions configured to be at least partially positioned below the chin and lower jaw of a wearer. The chin support member may comprise a pair of pivotable connections coupling the chin side portions to the main side portions and a height adjustment member extending externally through the height adjustment aperture of the main collar body. The collar may also comprise a locking member positioned around the height adjustment member external to the height adjustment aperture. This locking member may be adjustable relative to the height adjustment member between a first position and a second position, wherein in the first position, pivoting movement of the chin support member relative to the main collar body around the pair of pivotable connections is permitted, and wherein in the second position, pivoting movement of the chin support member relative to the main collar body is inhibited.

In some cases, the locking member may prevent the height adjustment member from withdrawing through the height adjustment aperture. the height adjustment member may also snap-fit through the locking member. The locking member may also be rotatable around the height adjustment member between the first position and the second position. In some arrangements, the locking member may be rotatable from the first position to the second position in only one direction of rotation.

When the locking member is in the first position, the height adjustment member may be at least partially withdrawable through the height adjustment aperture, and when the locking member is in the second position, the height adjustment member may not be withdrawable through the height adjustment aperture.

The height adjustment member may further comprise a tab extending radially from the height adjustment member. The tab may be spaced from the locking member when the locking member is in the first position, and the tab may be in contact with the locking member when the locking member is in the second position. In another embodiment, the locking member may comprise a first surface and a second surface, wherein each of the first and second surfaces may be selectively rotatable into alignment with the at least one tab, the second surface being externally raised relative to the first surface. Additionally, the tab may be inwardly compressible toward a central axis of the height adjustment member.

In another embodiment, the main collar body may further comprise a first ridged surface and the chin support member may further comprise a second ridged surface, wherein when the locking member is in the first position, the first and second ridged surfaces may be relatively slidable over each other, and when the locking member is in the second position, the first and second ridged surfaces may not be relatively slidable. The first and second ridged surfaces may not relatively slidable over each other between a plurality of adjusted positions.

The collar may further comprise a back panel member coupled to the main side portions of the main collar body. Furthermore, the pair of pivotable connections may removably secure the main collar body and chin support member together. The chin support member and main collar body may be separable from each other upon relative rotation to a predetermined position.

According to another aspect of the present disclosure, a method of manufacturing a height-adjustable cervical collar may be provided, comprising: providing a pivotal connection between a chin support member and a main collar body of a cervical collar; inserting a height adjustment member of the chin support member through a height adjustment aperture in the main collar body; and positioning a locking member around the height adjustment member such that the locking member is movable relative to the height adjustment member between a first relative position and a second relative position.

The method may further comprise pivoting the pivotal connection while the locking member is in the first relative position and inhibiting rotation of the pivotal connection while the locking member is in the second relative position. Rotation may be inhibited by ridges on the chin support member and the main collar body being pressed into an interlocking position interfering with rotation at the pivotal connection.

Positioning the locking member around the height adjustment member may comprise snap-fitting the height adjustment member with the locking member. The locking member may be positioned around the height adjustment member in a manner permitting rotation of the locking member around the height adjustment member. Additionally, the method may further comprise attaching a back panel member to the main collar body.

In another aspect, a cervical collar may be provided comprising: a lower support member configured to at least partially overlie the upper chest of a wearer that has a first ridged surface; an upper support member pivotally connected to the lower support member, wherein the upper support member has a second ridged surface facing the first ridged surface; and a releasable tensioning member connected to the cervical collar. The tensioning member may have an unlocked position and a locked position, wherein the unlocked position allows relative movement of the first and second ridged surfaces, and the locked position prevents relative movement of the first and second ridged surfaces by applying tension driving the first and second ridged surfaces into contact.

The tensioning member may be attached to or integrated with at least one of the lower and upper support members. The tensioning member may be removable from the at least one of the lower and upper support members.

Furthermore, the tensioning member may be rotatable between the locked and unlocked positions. Movement of a surface of the tensioning member may drive the first and second ridged surfaces into contact. The first and second ridged surfaces may be lockable in a plurality of positions relative to each other. The plurality of relative positions may correspond with a plurality of positions of the chin of a wearer.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1A:
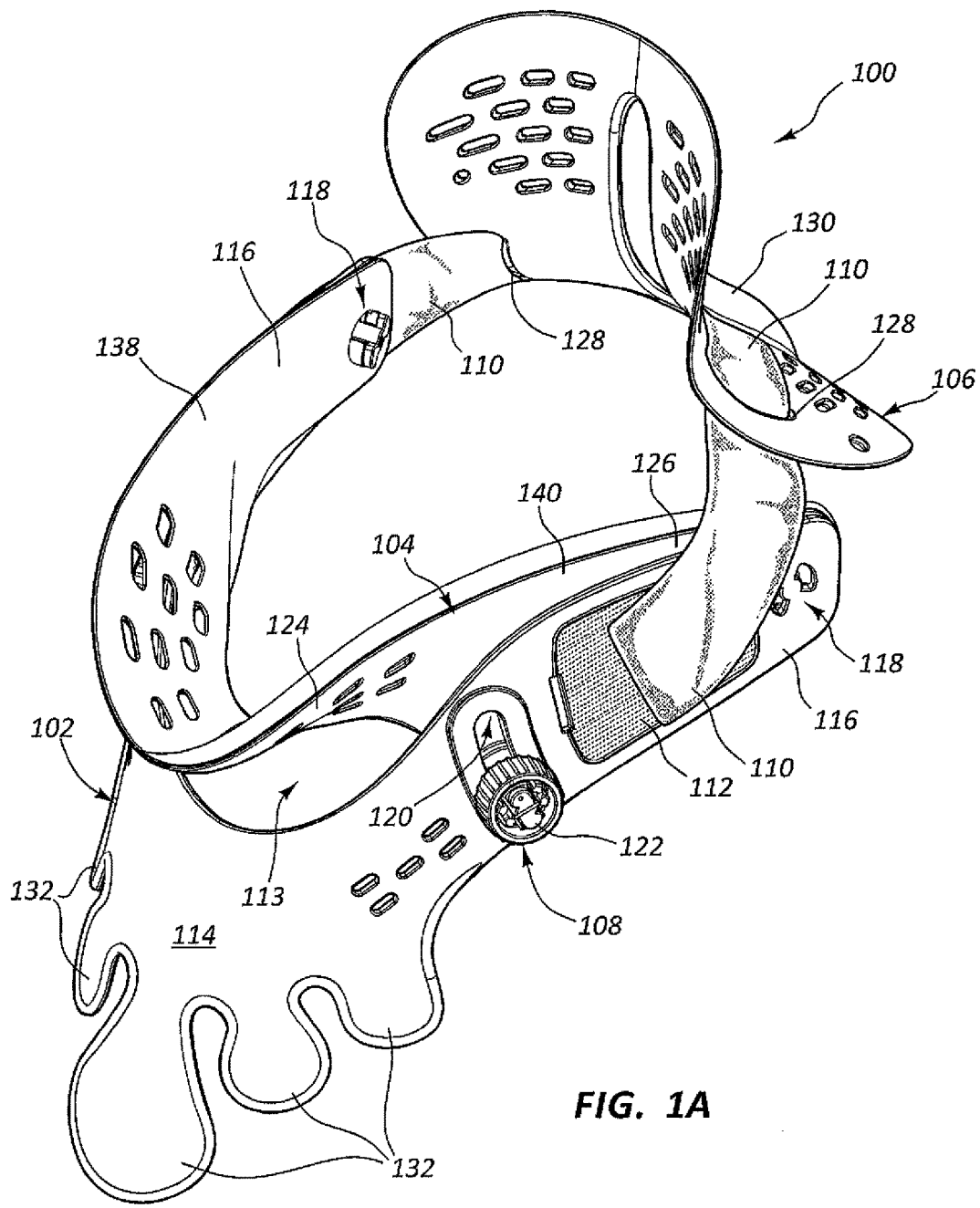
FIGS. 1A-1D are various views of an embodiment of a cervical collar according to the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Embodiments of the present disclosure may improve comfort and adjustability of cervical collars while remaining simple in operation and low in cost. According to one embodiment, a height-adjustable cervical collar may include a main collar body and a chin support member. The height of the front of the chin support member relative to the front of the main collar body may be pivotally adjusted around a pair of pivot points linking the sides of the main collar body and the chin support member. The chin support member may be secured in a desired position that provides a custom fit for a wearer and that provides the proper angle of orientation of the head relative to the neck and upper torso.

Ridges may be provided on opposing surfaces of the chin support member and the main collar body that interlock in a plurality of positions corresponding to various heights of the front of the chin support member. These ridges may be made either relatively slidable or relatively immobilized upon movement of a tensioning member or locking member. The tensioning or locking member may provide a secure, durable lock for the cervical collar that is inexpensive and easy to operate even by the patient while wearing the collar.

In one embodiment, the height adjustment of the cervical collar may be limited by movement of a height adjustment member traveling within the bounds of a height adjustment aperture. Typically, the height adjustment member extends from the chin support member externally through a height adjustment aperture in the main collar body. The tensioning or locking member may then snap-fit over the height adjustment member external to the height adjustment aperture in a manner preventing withdrawal of the member through the aperture. Thereafter, movement of the tensioning or locking member, such as, for example, rotational movement, may cause the opposing ridges on the main collar body and chin support member to interlock and prevent chin height adjustment.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Figure 1B:
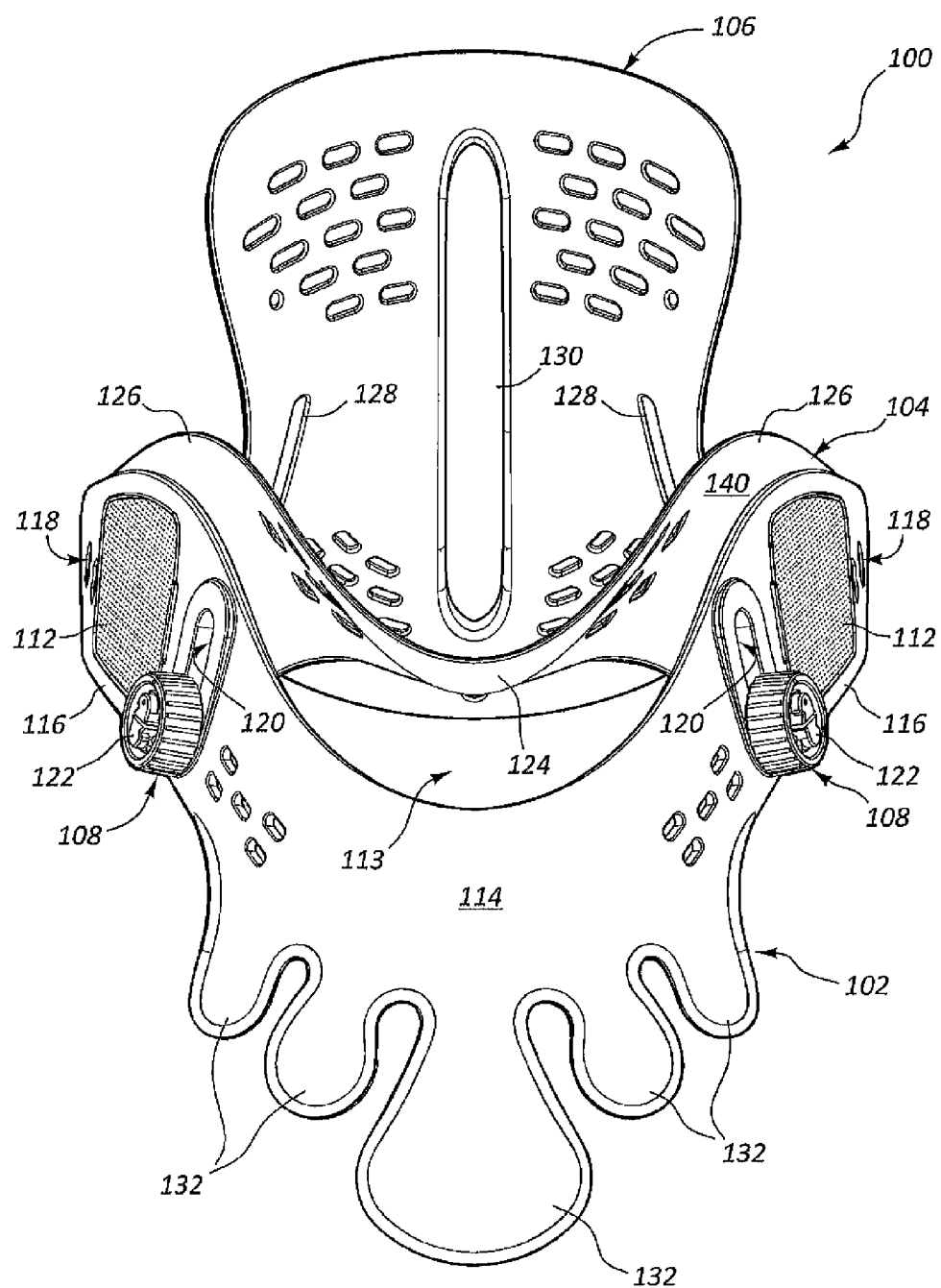
Figure 1C:
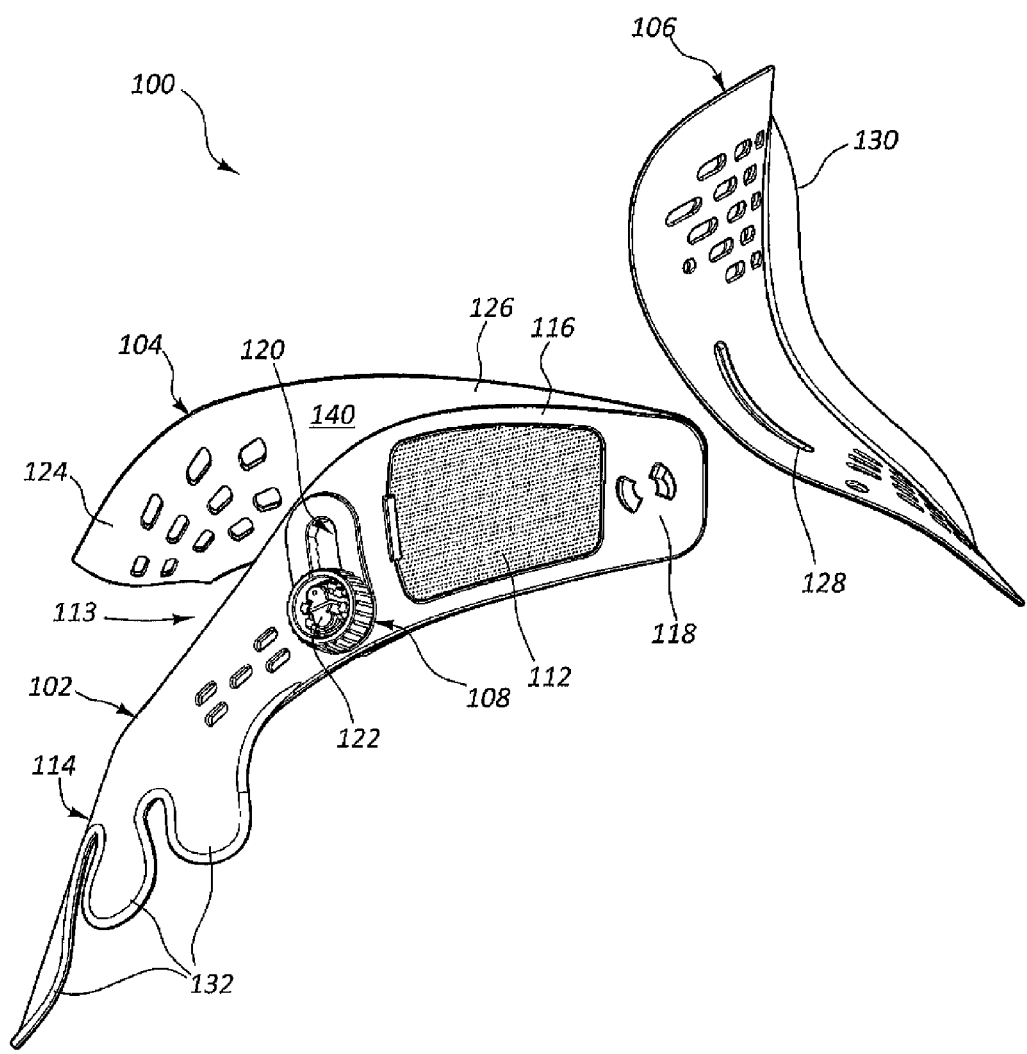
Figure 1D:
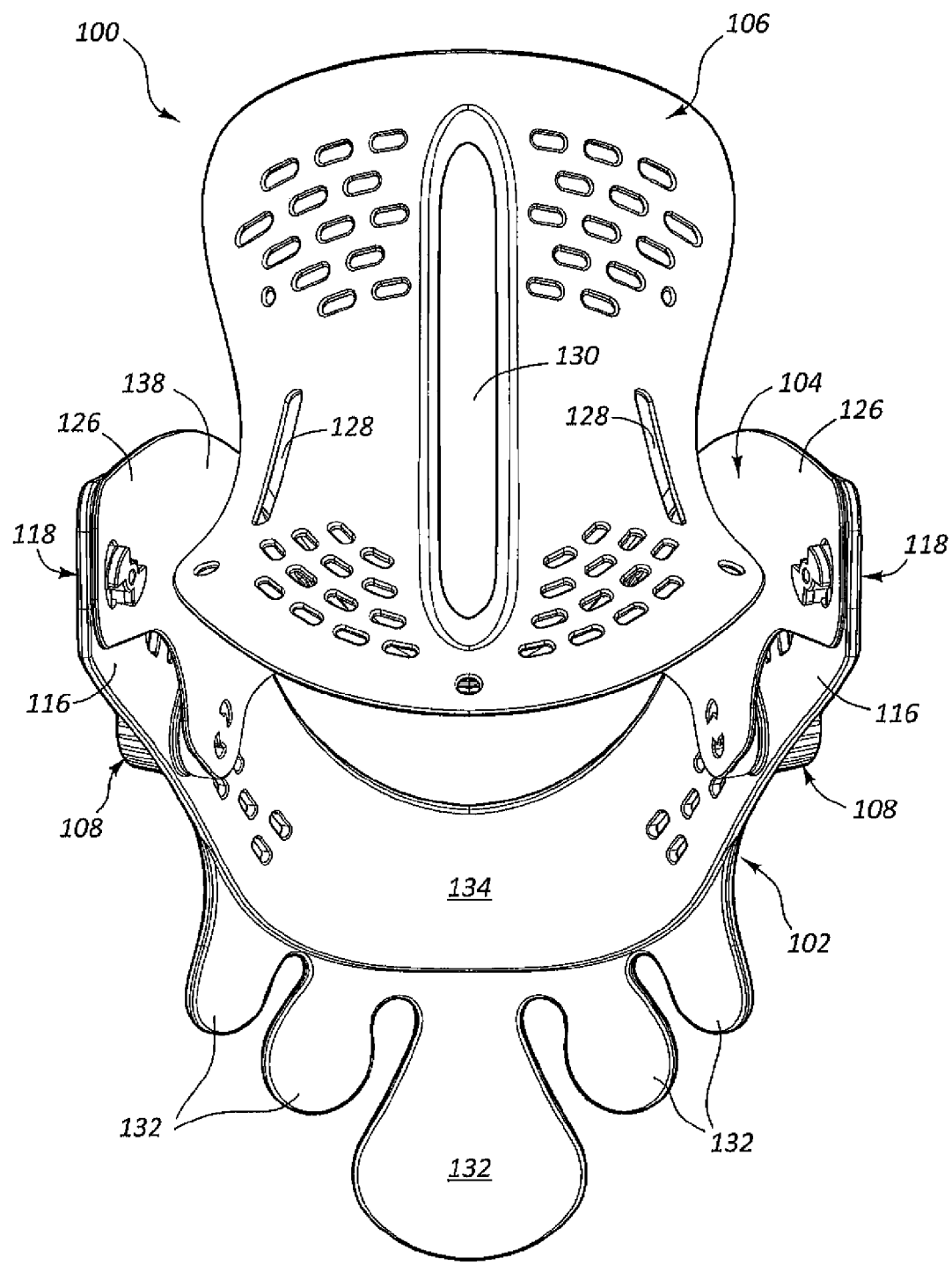

Referring now to the figures in detail, FIGS. 1A-1D show various views of an exemplary embodiment of a cervical collar 100 of the present disclosure. FIG. 1A is a perspective view, FIG. 1B is a front view, FIG. 1C is a side view, and FIG. 1D is a rear view. The cervical collar 100 may include a main collar body 102, a chin support member 104, and a back support member 106. The main collar body 102 and chin support member 104 may be linked using one or more locking members 108 and pivotal connections 118. The main collar body 102 and the back support member 106 may be linked using hook and loop fastener material, such as a hook and loop fastener strap 110 attached to the back support member 106 and a hook and loop fastener pad 112 attached to the main collar body 102.

The cervical collar 100 may be worn around the neck of a patient. See, e.g., FIG. 3. The main collar body 102 may be positioned against the anterior upper chest or lower neck area of the wearer, the back support member 106 may be positioned to the rear of the neck, preferably to the rear of the cervical vertebrae of the neck, and strapped to the main collar body using the hook and loop fastener material 110, 112. The chin support member 104 may be positioned at least partially within and above the main collar body 102, so as to support the chin, jaw, upper neck, and lower skull of the wearer. The chin support member 104 and main collar body 102 may define an open space 113 to be positioned at the tracheal area of the neck. This open space 113 may improve comfort, facilitate an open tracheal airway, and allow airflow to the skin of the neck. The height of the chin support member 104 may be referred to as the relative distance between a front portion 124 of the chin support member 104 and a front portion 114 of the main collar body 102. A lower height is a smaller distance between the front portions 114, 124, and a higher or taller height is a larger distance between them. The connections between the main collar body 102 and chin support member 104 may provide adjustable height between these front portions 114, 124, as described in further detail herein. Thus, using the pivotal connections 118 and the hook and loop fastener material 110, 112, the cervical collar 100 may provide a custom fit of the height of the chin support member 104 and of the distance between the main collar body 102 and the back support member 106, respectively.

The main collar body 102, chin support member 104, back support member 106, and locking member 108 may beneficially comprise a generally rigid material, such as a polymer or composite material. Such materials may beneficially reduce the weight of the cervical collar 100 and decrease manufacturing costs. They may also be partially flexible to improve comfort when wearing the collar 100.

The main collar body 102 may be referred to as a lower support member due to being positioned in the lower portion of the collar 100, the chin support member 104 may be referred to as an upper support member due to being positioned in an upper portion of the collar 100, and the locking member 108 may be referred to as a releasable tensioning member due to its function in tensioning the chin support member 104 and main collar body 102 together.

The cervical collar 100 may further comprise padding on internal surfaces of the main collar body 102, chin support member 104, and back support member 106. The padding may be removably securable to the rigid components of the cervical collar 100 by hook and loop fastener pads on the rigid components and/or the padding. In other arrangements, the padding may be secured to the collar 100 by adhesives or straps (e.g., FIG. 3 and related description).

The main collar body 102 may have a front portion 114 and side portions 116. The side portions 116 may be configured to extend around and provide support to the left and right sides of the neck (i.e., the lateral sides of the neck). The side portions 116 may include a pair of pivotal connections 118. In the embodiments of FIGS. 1A-1D, the pivotal connections 118 may be positioned at the back ends of the side portions 116 of the main collar body 102. In other cases, the pivotal connections 118 may be arranged farther toward the front portion 114 of the main collar body 102. The main collar body 102 may also comprise one or more height adjustment aperture 120 extending through one or more of the side portions 116. A height adjustment aperture 120 may be an opening through a side portion 116 that permits a height adjustment member 122 to externally extend through the main collar body 102 and translate through the height adjustment aperture 120 relative to the main collar body 102, as discussed in further detail elsewhere herein. A hook and loop fastener pad 112 may also be positioned on a side portion 116. The main collar body 102 may also comprise front flanges 132.

The chin support member 104 may link to the main collar body 102 at the pivotal connections 118 and via the height adjustment apertures 120. The chin support member 104 may comprise a pair of height adjustment members 122 extending through the height adjustment apertures 120 and slidable within the height adjustment apertures 120. In conjunction with the pivotal connections 118, the chin support member 104 may thus tilt or rotate along a path defined by travel of the height adjustment members 122 along the height adjustment apertures 120. The height adjustment members 122 may be prevented from withdrawal through the height adjustment apertures 120 by interference with the locking members 108 and/or by tabs extending radially from the end of the members 122. See, e.g., tabs 550 in FIG. 5. The side portions 126 of the chin support member 104 may comprise indicator lines or guides that indicate to the user of the cervical collar 100 the relative rotated positions of each side portion 126 relative to the adjacent side portion 116 of the main collar body 102. Using the guide lines, a user may determine if each side is raised or lowered to the same distance, so the wearer's comfort may be improved due to the left and right sides of the head being supported at the same angle.

In some cases, the side portions 126 of the chin support member 104 may be positioned external to the side portions 116 of the main collar body 102. In these cases, the height adjustment aperture 120 may be formed in the chin support member 104 and the height adjustment member 122 may be formed on the main collar body 102.

The main collar body 102 may have an internal surface 134 and an external surface 136. The internal surface 134 may comprise a plurality of inward-facing ridges 142. See FIGS. 2 and 4A. The chin support member 104 also may have an internal surface 138 and an external surface 140. The external surface 140 may face the internal surface 134 of the main collar body 102. The external surface 140 may also comprise a plurality of ridges 144 sized and positioned to interact with the plurality of ridges 142 on the main collar body 102. See FIG. 5. In the embodiment of FIGS. 1A-1D, the ridges 142, 144 are positioned adjacent to the height adjustment aperture 120 and height adjustment member 122, but in other embodiments, the ridges may be configured elsewhere along the side portions 116 of the main collar body 102 and side portions 126 of the chin support member 104 where the ridges can interlock with each other when the height adjustment member 122 is drawn outward relative to the height adjustment aperture 120. When pressure is not being applied by the height adjustment member 122 to drive the external surface 140 toward the internal surface 134, the ridges 142, 144 may slide over each other in a direction about perpendicular to the parallel lines formed by the ridges. Thus, the ridges 142, 144 may be repositioned relative to each other, and if they are locked in place again in a new position, the chin support member 104 and main collar body 102 will also have new relatively pivoted positions. In this manner, the cervical collar 100 may be adjusted to support the neck at various raised or lowered positions.

The back support member 106 may be positioned behind the neck of the wearer. The back support member 106 may include apertures 128 through which hook and loop fastener straps 110 may be attached. The back support member 106 may also include a back groove 130 positioned vertically along a substantial portion of the height of the back support member 106. The back groove 130 may improve comfort of the back support member 106 by providing a recess in which the surface of the neck adjacent to the spinous processes of the cervical vertebrae may be received. The back support member 106 may be curved to follow a predefined contour aligning the cervical vertebrae in a desired orientation to be held by the cervical collar 100 in general.

The locking member 108 may be a releasable securing means for holding the orientation of the chin support member 104 relative to the main collar body 102. Embodiments of the locking member 108 are described and shown in greater detail in FIGS. 7A-8B. The locking member 108 may releasably drive the ridges 142, 144 into contact with each other, thereby locking the height of the chin support member 104 at a desired position. In some embodiments, the ridges 142, 144 may interlock in this position, meaning they have corresponding surfaces that fit together adjacent to each other. The locking member 108 may also be moved to a position where it does not drive the ridges 142, 144 into contact such that the ridges 142, 144 are relatively slidable or liftable over each other. In this position, the height of the chin support member 104 may be adjusted until the locking member 108 is moved to a position where the ridges 142, 144 are driven back into contact with each other.

Figure 4A:
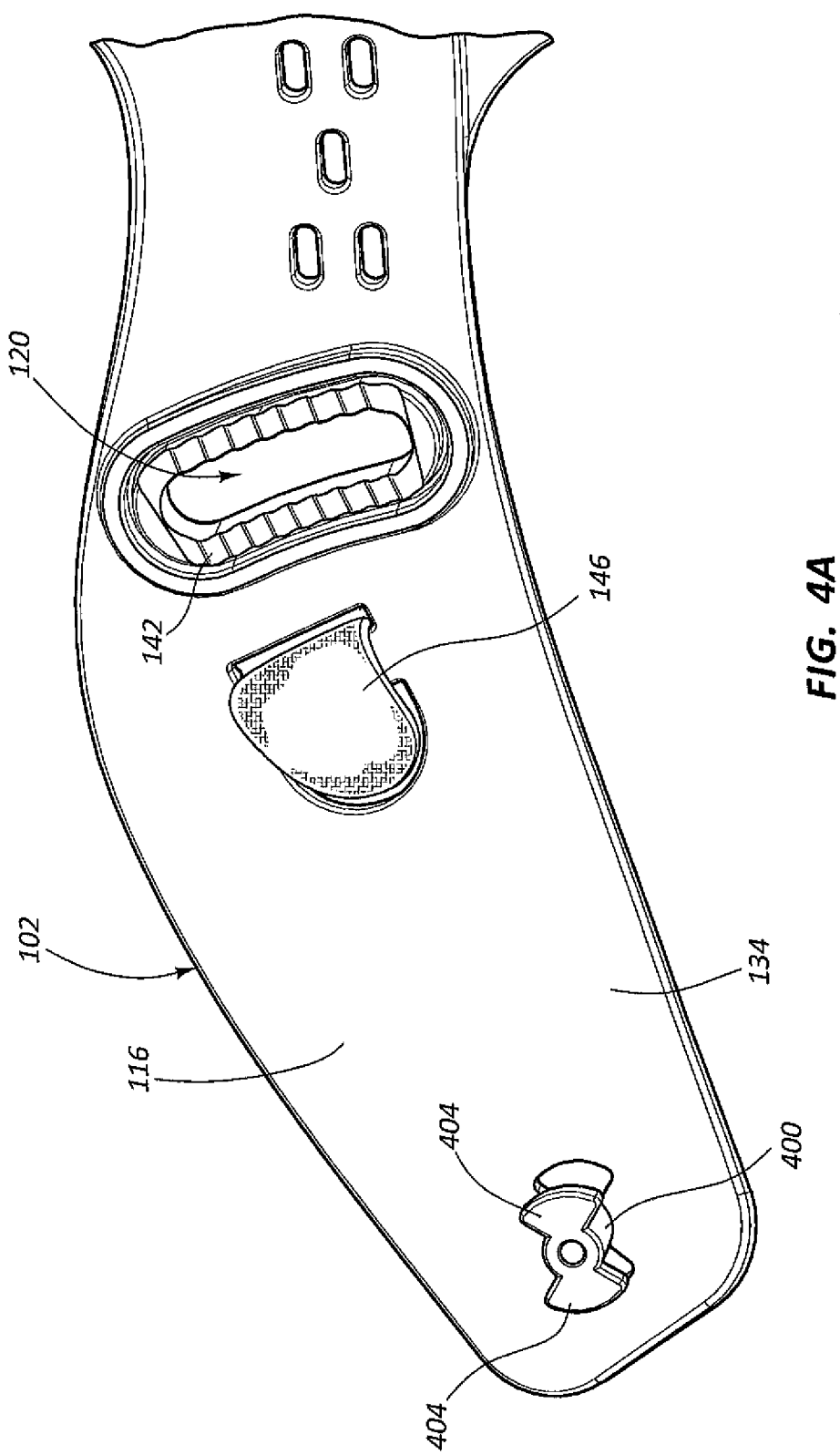
FIG. 4A is a view of the inside of a main collar body of an embodiment of a cervical collar according to the present disclosure.

A hook and loop fastener strap 110 and pad 112 may allow the back support member 106 to be adjusted in horizontal and vertical directions relative to the main collar body 102. The straps 110 and pads 112 may also adjust the tightness of the cervical collar 100 around the wearer's neck. The use of hook and loop fastener material may easily allow small or large adjustments to the fit of the collar 100, and may allow the collar 100 to be moved or removed by the wearer. Other connecting means may also be used, such as ratcheting plastic straps, interlocking parts, hooks extending between the side portions 116 and the back support member 106, or another similar means apparent to those skilled in the art having the benefit of the present disclosure. A pad 112 on the main collar body 102 may be beneficially placed on the side portions 116 where at least a portion of the anterior end of the pad may be directed through the main collar body 102. This anterior portion 146 may extend through the main collar body 102 and attach or adhere to the back of the pad 112, as shown in FIG. 4A. With the anterior portion 146 thus configured, the pad 112 may be reinforced against becoming pulled from the main collar body 102 when the front end of a strap 110 is pulled away from the main collar body 102.

The pivotal connections 118 may be positioned at the back ends of the side portions 116, 125 of the main collar body 102 and chin support member 104. The pivotal connections 118 may be removably securable or non-removable. For example, non-removable pivotal connections 118 may be rivets or another at least somewhat permanent connection means keeping the chin support member 104 and main collar body 102 connected but still allowing relative height adjustment of their front portions 114, 124. See, e.g., FIG. 3. The pivotal connections 118 may be removably secured by structures such as a bolt and nut or by a rotation lock such as the elements shown in FIGS. 1A-1D. Elements of an embodiment of a pivot lock are shown in detail in FIGS. 4A-4B and described below.

The height adjustment aperture 120 may comprise openings through the main collar body 102 on the side portions 116. In the embodiments shown, the main collar body 102 comprises two height adjustment apertures 120, but in other embodiments, one or more than two apertures may be formed according to the needs of the designer. Height adjustment apertures 120 may beneficially be formed adjacent to or within the portions of the internal surface 134 having ridges 142. This may allow the movement of the height adjustment member 122 inward and outward in the height adjustment aperture 120 to more directly affect the position of the ridges 142 relative to ridges 144 on the chin support member 104 than ridges positioned farther from the aperture 120, such as near the pivotal connections 118 or front portion 114. In other words, relative movement of the ridges 142, 144 may be more directly enacted by relative movement of the height adjustment member 122 in the aperture 120 when the ridges 142, 144 are adjacent to the member 122 and aperture 120. The shape of the height adjustment apertures 120 may beneficially follow the paths of motion of the height adjustment members 122 as they rotate around the pivotal connections 118 while extending through the main collar body 102. The terminal ends of the apertures 120 may define the limits of adjustment of the height of the chin support member 104 to positions commonly used among patients. In some embodiments, the height adjustment apertures 120 may be holes, openings, passages, slots, or channels in the main collar body 102.

Height adjustment members 122 may extend from the external surface 140 of the chin support member 104 through the height adjustment apertures 120 of the main collar body 102. In other embodiments, the internal surface 138 of the chin support member 104 may be positioned external to the external surface 136 of the main collar body 102, and the height adjustment members 122 may extend from the external surface 136 of the main collar body 102 through apertures that extend through the chin support member 104. Height adjustment members are also discussed in detail in connection with FIGS. 2 and 5, infra.

The front flanges 132 may provide flexible support for the main collar body 102 against the wearer's upper torso. Broad, curved flanges 132 may distribute pressure on the wearer's torso and improve comfort of the collar 100. The front flanges 132 may also provide a design element to improve the cosmetic and aesthetic appeal of the collar 100.

Figure 2:
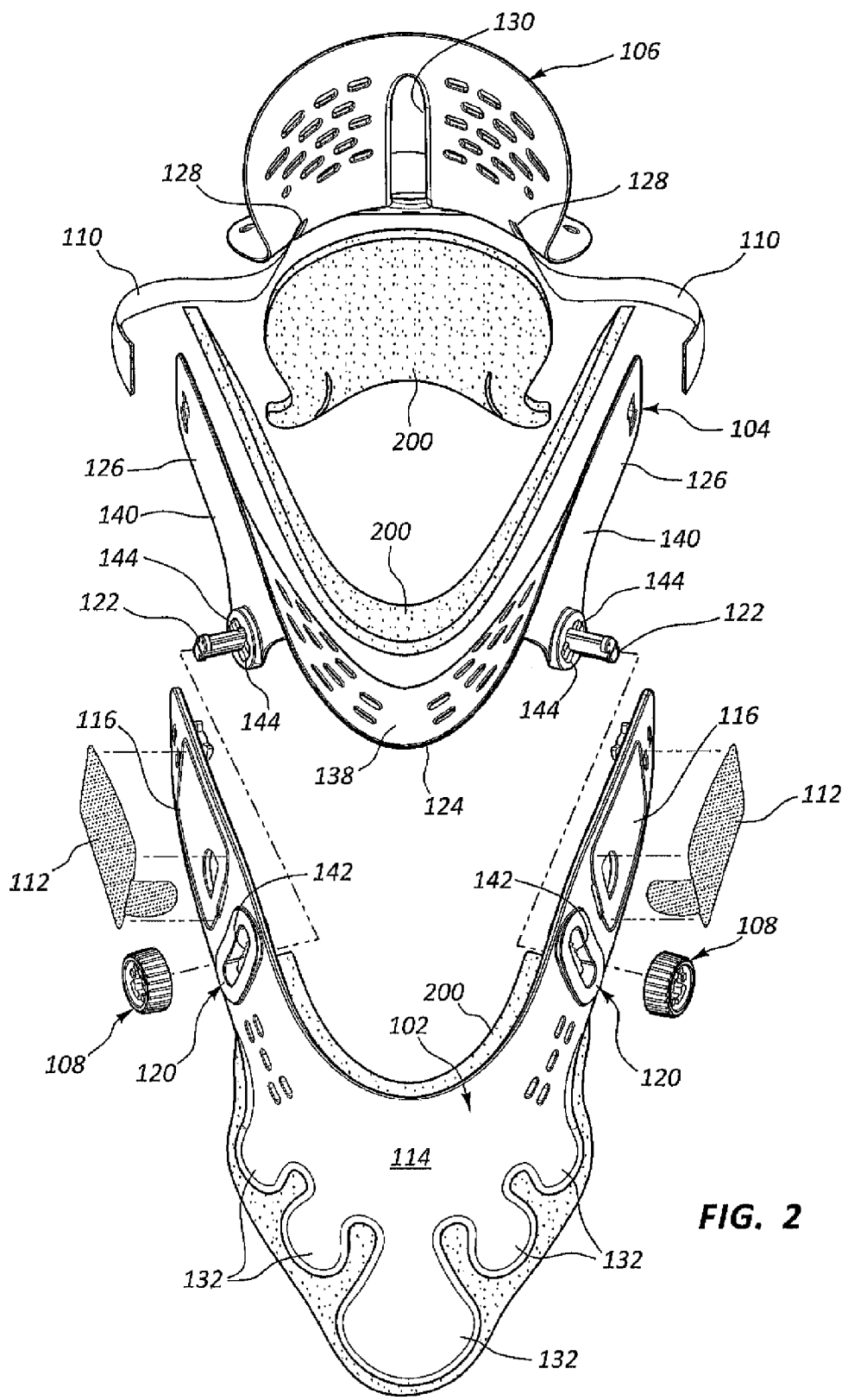
FIG. 2 is an exploded view of the cervical collar of FIG. 1A.

FIG. 2 is an exploded view of the cervical collar 100. The interaction and relative positioning of many features of the embodiment described in connection with FIGS. 1A-1D is shown in FIG. 2. The exploded view shows ridges 144 on the chin support member 104 adjacent to the height adjustment member 122 extending from the external surface 140. The ridges 144 may correspond with ridges 142 on the internal surface 134 of the main collar body 102 adjacent to the height adjustment apertures 120. See also FIGS. 4A and 6A-6B. This view also shows exploded positions of padding 200 for the cervical collar 100.

Figure 3:
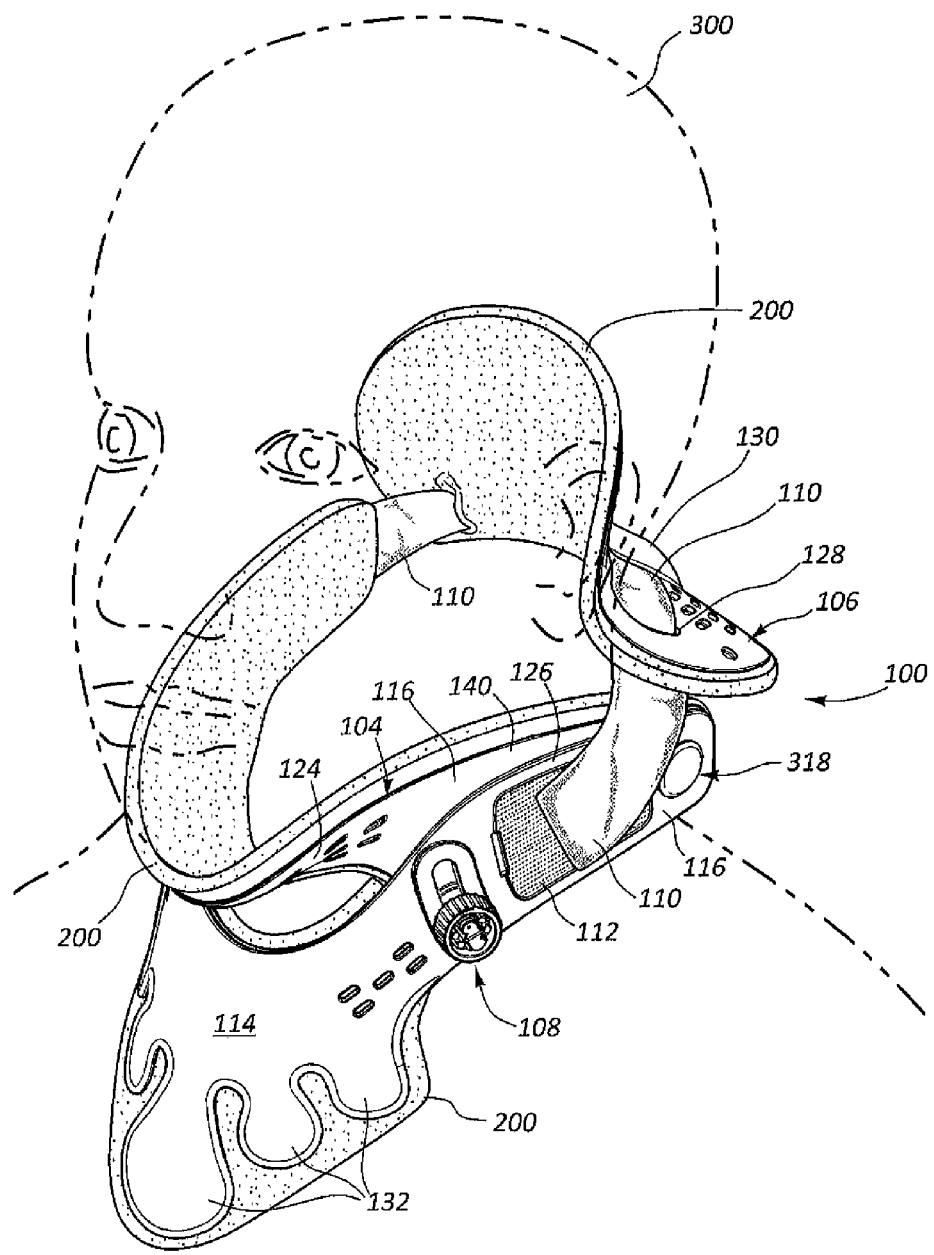
FIG. 3 is a view of the cervical collar of FIG. 1A being worn by a patient.

FIG. 3 shows an exemplary embodiment where the cervical collar 100 is worn by a patient 300. The padding 200 may protect the skin of the patient 300 from chafing or scratches by the relatively rigid material used to make other parts of the cervical collar 100 that would contact the patient 300. This view also shows an alternative embodiment of the pivotal connection 318 between the main collar body 102 and the chin support member 104. In this embodiment, the pivotal connection 318 is a rivet or other similar permanent connection that permits pivotal movement between the parts 102, 104 while securing them together without being removable simply by relative rotation of the parts 102, 104.

The foam padding 200 may protect the wearer 300 by dampening and cushioning relative movements between the cervical collar 100 and the wearer 300. The padding 200 may improve comfort, especially when the collar 100 is worn over long periods of time. The padding 200 may comprise foam rubber, neoprene, or another comfortable, elastically-flexible synthetic or natural padding material. In conjunction with the hook and loop fastener material 110, 112 and the height adjustment between the chin support member 104 and main collar body 102, the padding 200 may provide an additional amount of comfort and customizability to the cervical collar 100. For example, the thickness or material of the padding 200 may be changed to affect the rigidity of the foam or the distance between the internal surfaces of the collar 100 and the wearer's body.

Figure 4B:
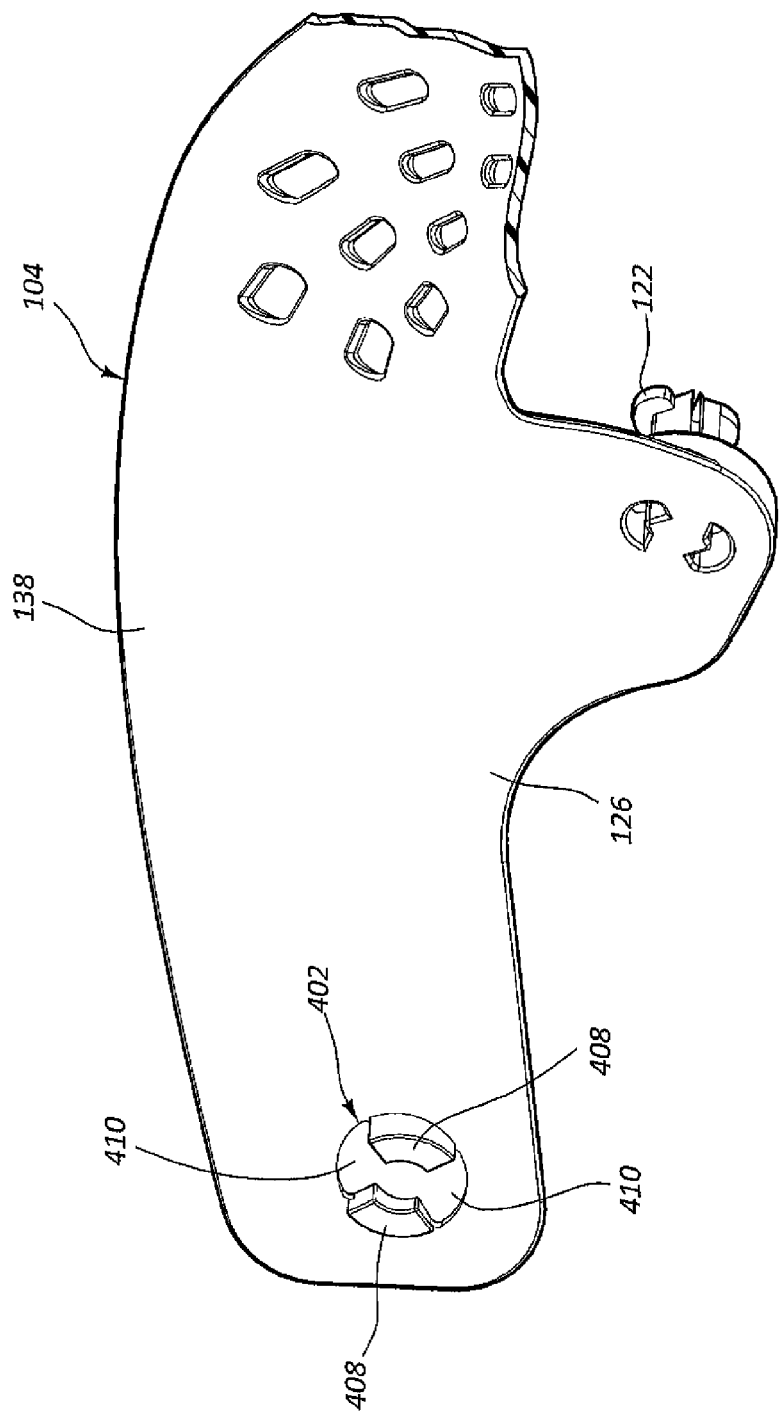
FIG. 4B is a view of the inside of a chin support member of an embodiment of a cervical collar according to the present disclosure.

FIGS. 4A-4B show internal surfaces 134, 138 of the main collar body 102 and chin support member 104. FIG. 4A shows ridges 142 extending from the internal surface 134 of the main collar body 102 around the height adjustment aperture 120. The height adjustment aperture 120 may have an elongated shape to allow ridges 144 adjacent to a height adjustment member 122 to be seated in a range of positions relative to the aperture 120 as the chin support member 104 pivots about the pivotal connections 118. The ridges 142 may correspondingly extend around the perimeter of the height adjustment aperture 120 so that ridges 144 adjacent to the height adjustment member 122 on the chin support member 104 may be seated in at least some of the ridges 142 of the main collar body 102 at a plurality of pivoted positions of the chin support member 104. The ridges 142 may beneficially be formed and spaced so that the ridges 144 of the chin support member 104 may fit with the ridges 142 on the main collar body when the height adjustment member 122 is at the extreme ends of the elongated shape of the height adjustment aperture 120. Thus, the entire length of the elongated shape may provide the range of motion of the height adjustment member 522.

FIG. 4A also illustrates a pivot stem 400 extending from the side portion 116 of the main collar body 102. The pivot stem 400 may be configured to be inserted through a pivot opening 402 in a side portion 126 of the chin support member 104, thereby forming the pivotal connection 118 between the main collar body 102 and chin support member 104. The pivot stem 400 may comprise locking flanges 404 that extend radially outward from a central axis of the pivot stem 400. The flanges 404 may have increased circumferential width at their outermost radial surfaces as compared to their width near the central axis of the pivot stem 400. Thus, they may form the fan shapes shown in FIG. 4A.

FIG. 4B shows an internal surface 138 of a side portion 126 of a chin support member 104. A pivot opening 402 is shown in the side portion 126 that may be configured to receive a pivot stem 400 of the main collar body 102. To insert the pivot stem 400 through the pivot opening 402, the pivot stem 400 and pivot opening 402 would need to be in a relative rotated position where flange keyways 410 of the pivot opening 402 align with and receive the locking flanges 404. In this orientation, the pivot stem 400 may be moved through the pivot opening 402 and then be rotated so that the flanges 404 are internal to flange supports 408 extending inward from the internal surface 134 near the pivot opening 402. With the flanges 404 positioned inward from the internal faces of the supports 408, the pivot stem 400 may not be withdrawn through the opening 402 without reorientation of the flanges 404 to fit back through the keyways 410. The width of the flanges 404 and supports 408 may help ensure that the flanges 404 are not unintentionally withdrawn through the opening 402 over a wide range of relative pivoted angles of the main collar body 102 and the chin support member 104. In some embodiments, these angles may include up to 90 degrees of relative rotation of the respective side portions 116, 126 near the pivotal connections 118. In some embodiments, the flange-and-keyway design may allow the chin support member and the main collar body to be separated from each other after assembly if they are rotated to a predetermined position (e.g., the position they are in when the stem 400 is inserted through the opening 402).

Figure 5:
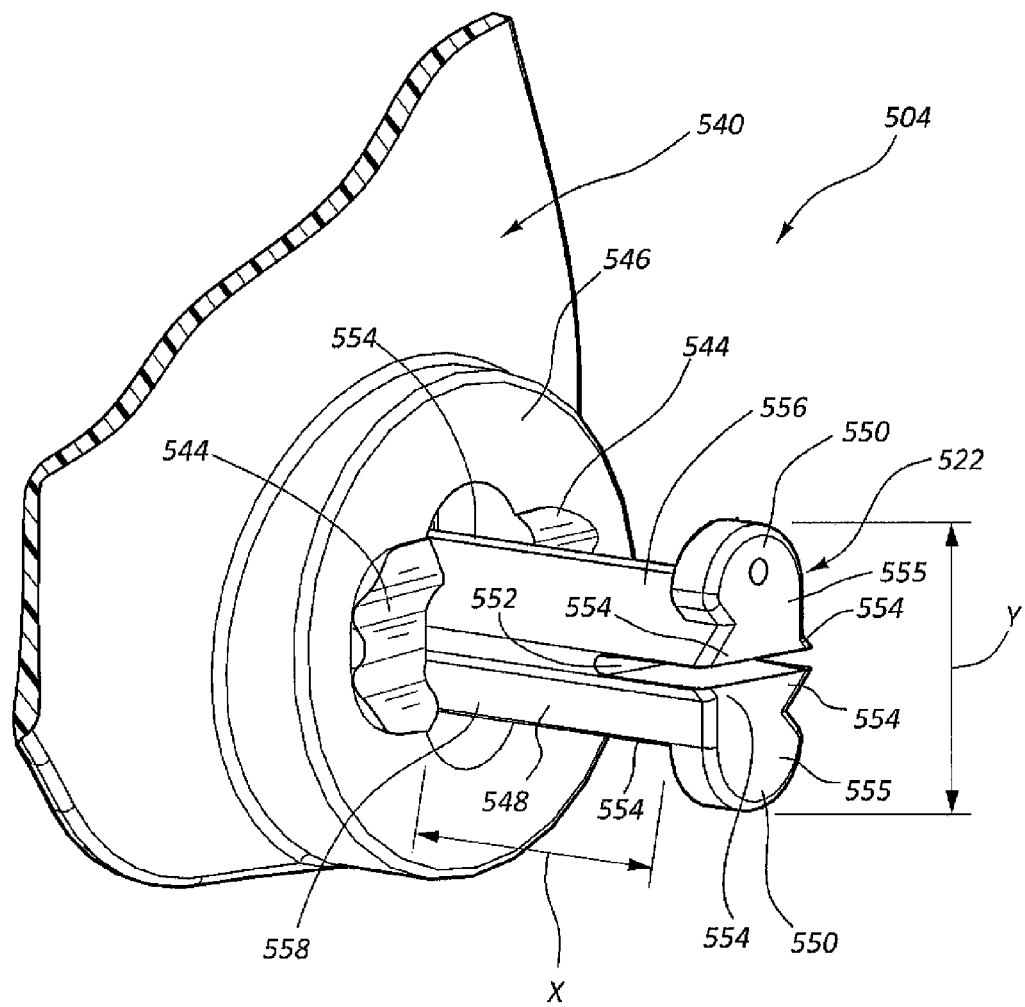
FIG. 5 is a detail external view of a chin support member of an embodiment of a cervical collar according to the present disclosure.

FIG. 5 shows a detailed view of a height adjustment member 522 extending from an external surface 540 of a chin support member 504. The height adjustment member 522 may be an embodiment of a height adjustment member 122 described above. As shown in this figure, the height adjustment member 522 may have an elongated shape extending from the external surface 540. In some embodiments, the external surface 540 may include a raised portion 546 separating the base of the height adjustment member 522 from the surrounding external surface 540 of the chin support member 504. The raised portion 546 may reduce contact and friction between the chin support member 504 and a main collar body (e.g., main collar body 102) by providing a surface separating the chin support member 504 and main collar body. Additionally, because the external surface 540 is curved in typical embodiments, the raised portion 546 may provide a flat surface against which the internal surface or ridges (e.g., ridges 142) of the main collar body can slide and directly interface. Thus, the raised portion 546 may establish a limit of penetration of the height adjustment member 522 through a height adjustment aperture (e.g., height adjustment aperture 120). Limiting the depth of penetration may beneficially prevent a locking member 108 from being too loose on the height adjustment member 522 to keep the ridges (e.g., ridges 142, 144) in contact when the locking member is in a locked position on the height adjustment member 522. The raised portion 546 may also include ridges 544 that interlock with or slide over ridges on a main collar body as the collar 100 is locked or adjusted.

The height adjustment member 522 may comprise a shaft 548 having a length X. Length X may extend from the raised surface 546 to the inner side of one or more tabs 550 radially extending from the shaft 548 at the end of the height adjustment member 522. The tabs 550 may have a width Y. In some embodiments, the external end of the height adjustment member 522 may include a flexure slot 522 allowing the tabs 550 to elastically flex inward, thereby temporarily reducing width Y.

The height adjustment member 522 may also comprise key ridges 554 on multiple sides of the shaft 548 and external end of the height adjustment member 522. In embodiments where the flexure slot 552 is not present, key ridges 554 may not be split in the manner shown in FIG. 5, but may instead be solid at the external end of the height adjustment member 522. Key ridges 554 may be beneficial in keeping a locking member (e.g., locking member 108) in a locked or unlocked position, as described in additional detail in connection with FIGS. 9A-12B.

The terminal end of the height adjustment member 522 may also comprise at least one indicator surface 555. The indicator surface 555 may have symbols printed, embossed, engraved, or molded onto it to help the user determine whether a locking member is in a locked position or an unlocked position. For example, when the locking member is in a locked position, an arrow (e.g., arrow indicator 822 of FIG. 8A or indicator 722 of FIG. 7A) or other symbol on the locking member may point toward a lock symbol on the indicator surface 555, and when the locking member is in an unlocked position, the arrow may not point toward the lock symbol (or vice versa).

The shaft 548 of the height adjustment member 522 may comprise at least four side surfaces, including at least two opposing permissive surfaces 556 and at least two restrictive surfaces 558 on other opposing surfaces. The permissive surfaces 556 may be generally positioned closer to a central axis of the shaft 548 than the restrictive surfaces 558. See, e.g., FIG. 9B, which shows a cross-section of the shaft 548. In one embodiment, the permissive surfaces 556 may be sloped (e.g., similar to sides of a diamond) relative to the central axis of the shaft 548, and the restrictive surfaces 558 may be corners or peaks (e.g., similar to corners of a square) relative to the central axis and compared to the permissive surfaces 556. With a locking member disposed around the shaft 548, the locking member may turn at least more easily between locked and unlocked positions around the permissive surfaces 556 than around the restrictive surfaces 558. This may beneficially control the amount of rotation of the locking member around the shaft 548. It may also help guide the user in determining which direction he should turn the locking member to lock or unlock the brace. See also FIGS. 9A-12B and their related descriptions below.

Figure 6A:
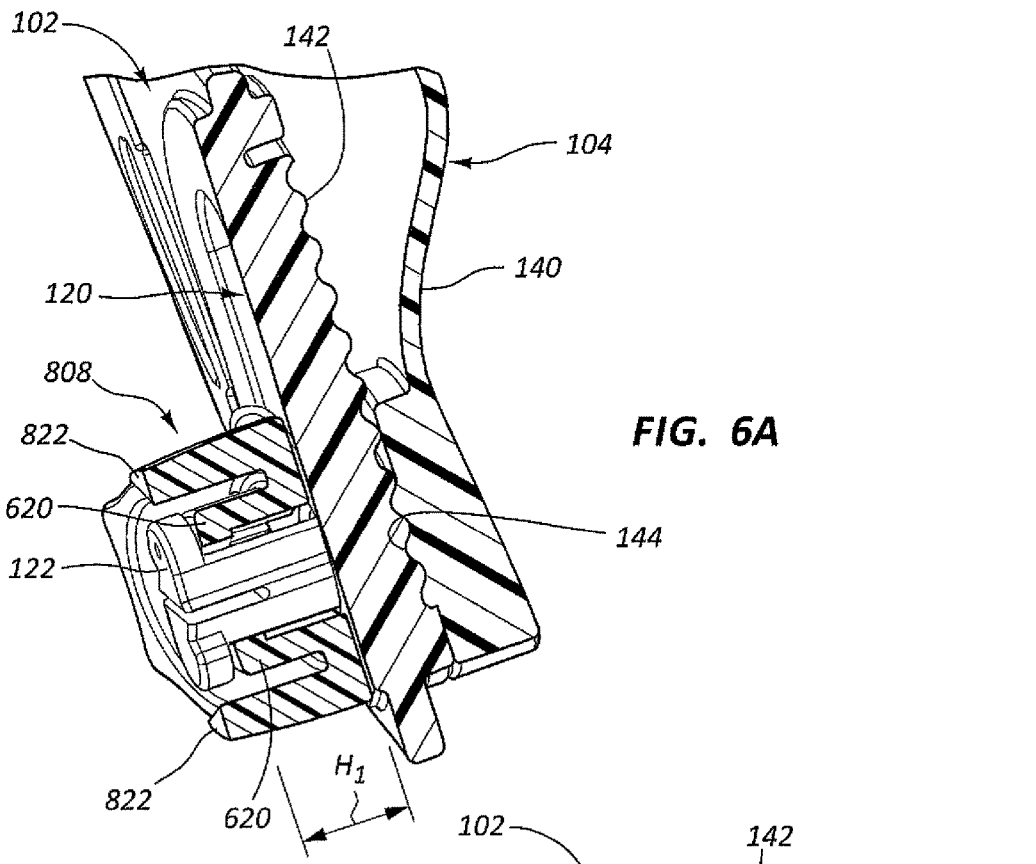
FIG. 6A is a section view of the interaction between locked ridges on a main collar body and a chin support member and between a height adjustment member and a locked locking member of a cervical collar according to the present disclosure.
Figure 6B:
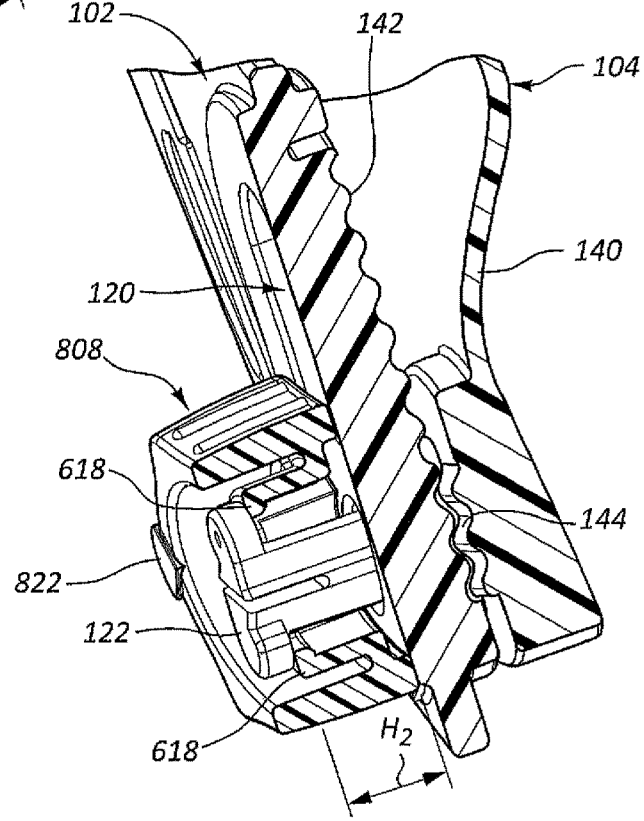
FIG. 6B is a section view of the interaction between unlocked ridges on a main collar body and a chin support member and between a height adjustment member and an unlocked locking member of a cervical collar according to the present disclosure.

FIGS. 6A-6B show a section view illustrating the interaction of the ridges 142, 144 relative to the positioning of a locking member 808. This locking member 808 is also shown in FIGS. 8A-8B. The locking member 808 may also be locking members 108 or 708. See FIG. 7A-7B. In FIG. 6A, the locking member 808 is in a locked position. The ridges 142, 144 are interlocked and are not slidable over each other because the height adjustment member 122 is fully inserted through the height adjustment aperture 120, as indicated by length $H_1$. The height adjustment member 122 cannot be withdrawn through the height adjustment aperture 120 in this position because locked position supports 620 are against the inside surfaces of tabs (e.g., tabs 550 of FIG. 5) at the end of the height adjustment member 122. Thus, the main collar body 102 and chin support member 104 are not relatively pivotable at this height adjustment aperture 120.

In FIG. 6B, the locking member 808 is in an unlocked position. The ridges 142, 144 can be separated (as shown) and can slide over each other because the height adjustment member 122 is partially withdrawn through the height adjustment aperture 120. The height adjustment member 122 now only has length $H_2$ extending out of the aperture 120, which is less than length $H_1$. The locking member 808 has been rotated about 90 degrees between FIGS. 6A and 6B, as shown by the rotation of the external indicators 822. See also FIGS. 9A and 11A. Thus, the locked position supports 620 are no longer positioned between the tabs of the height adjustment member 122 and the main collar body 102. Instead, in this position, unlocked position supports 618 are allowing the tabs to move closer to the height adjustment aperture 120, thereby providing slack between the ridges 142, 144. Additional details and embodiments of the locking member 808 are shown and described in connection with FIGS. 7A-8B.

Figure 7A:
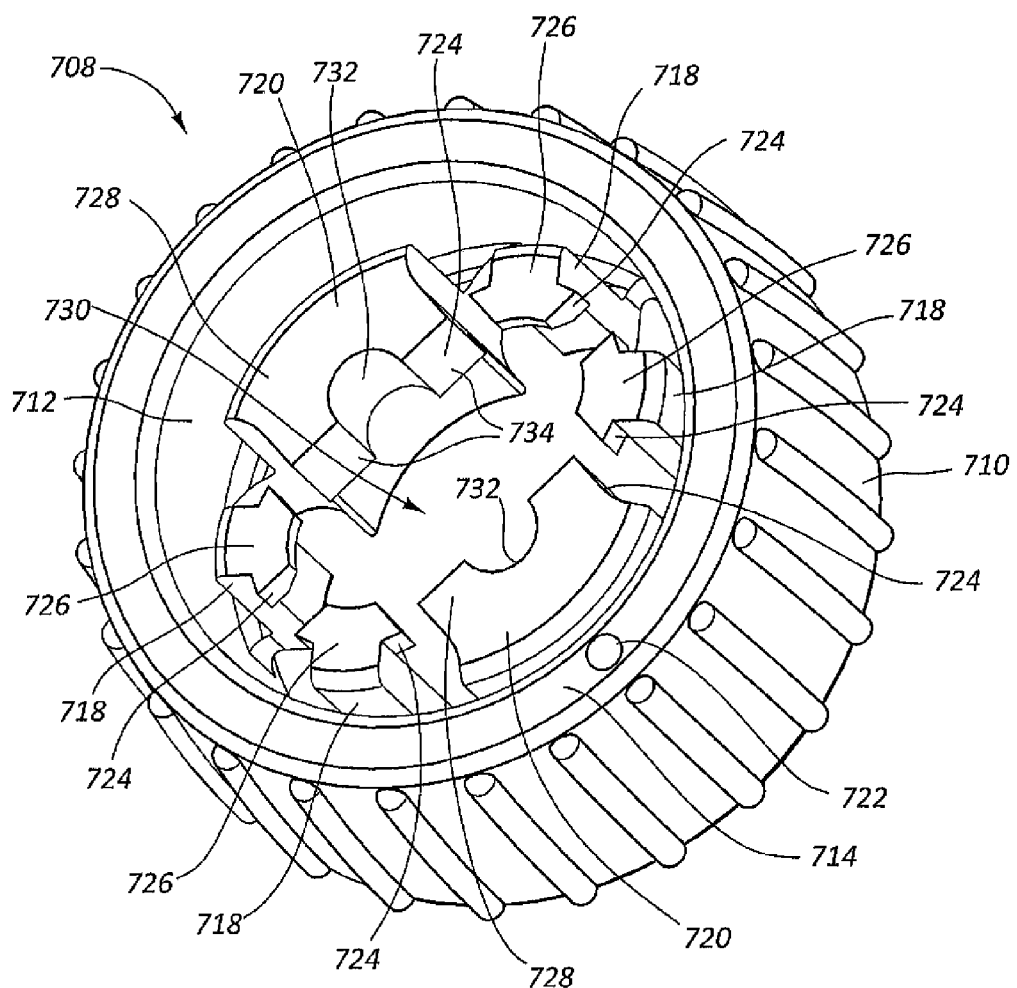
FIGS. 7A-7B are respective exterior and interior views of an embodiment of a locking member.
Figure 7B:
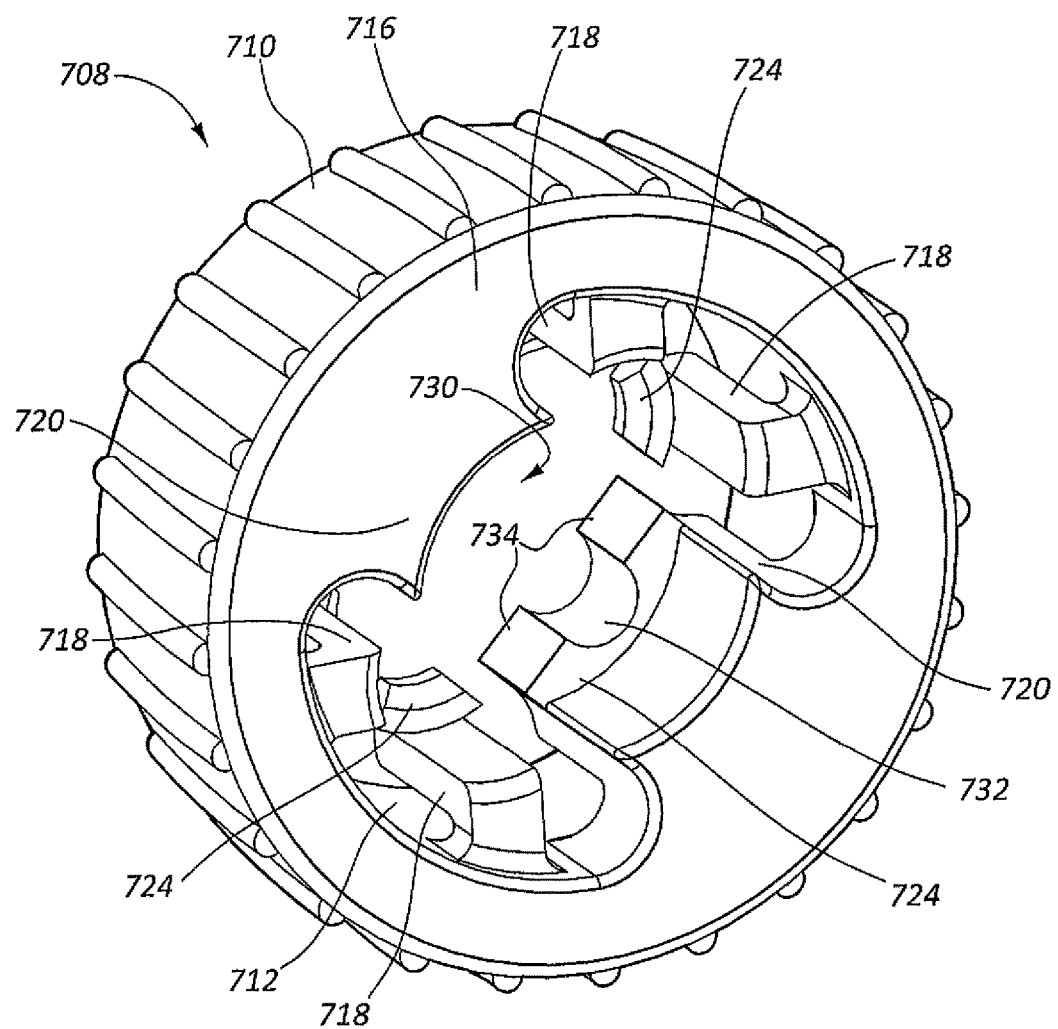
Figure 8A:
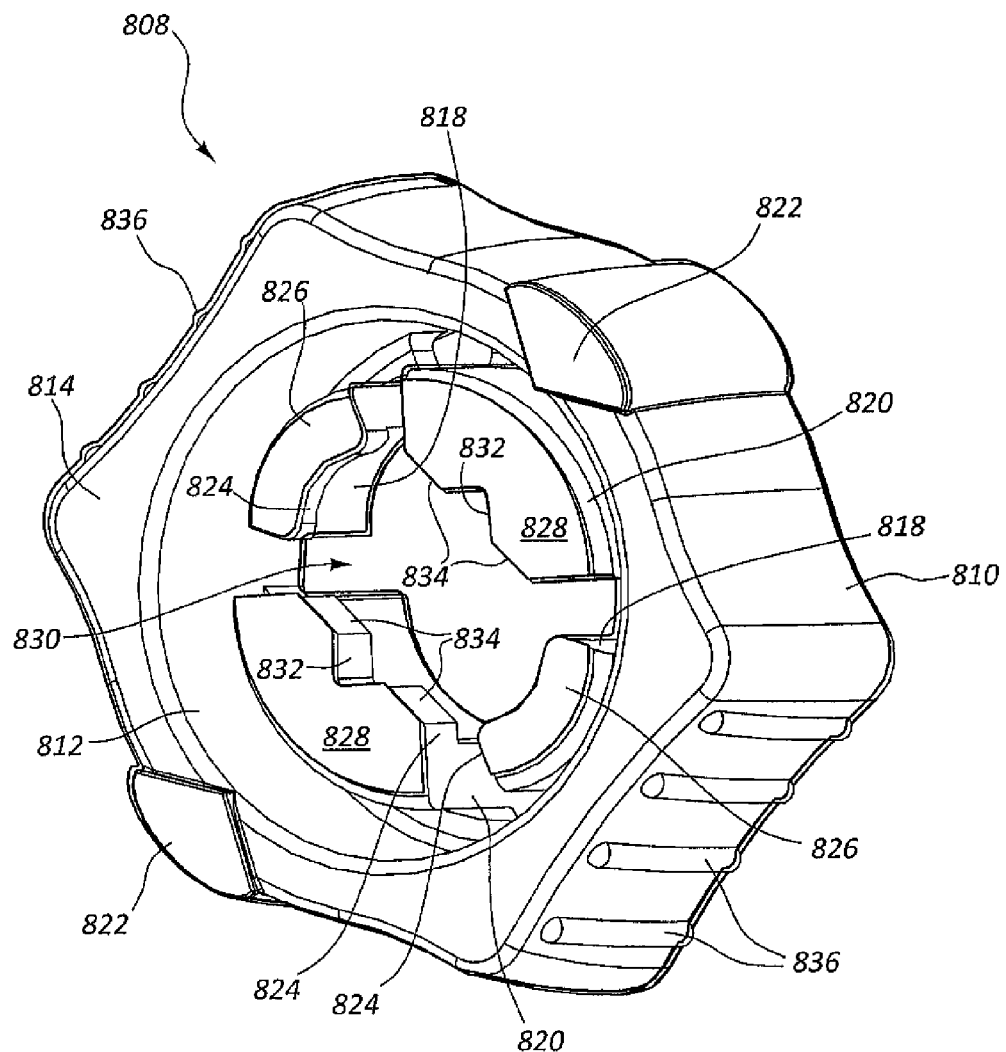
FIGS. 8A-8B are respective exterior and interior views of another embodiment of a locking member.
Figure 8B:
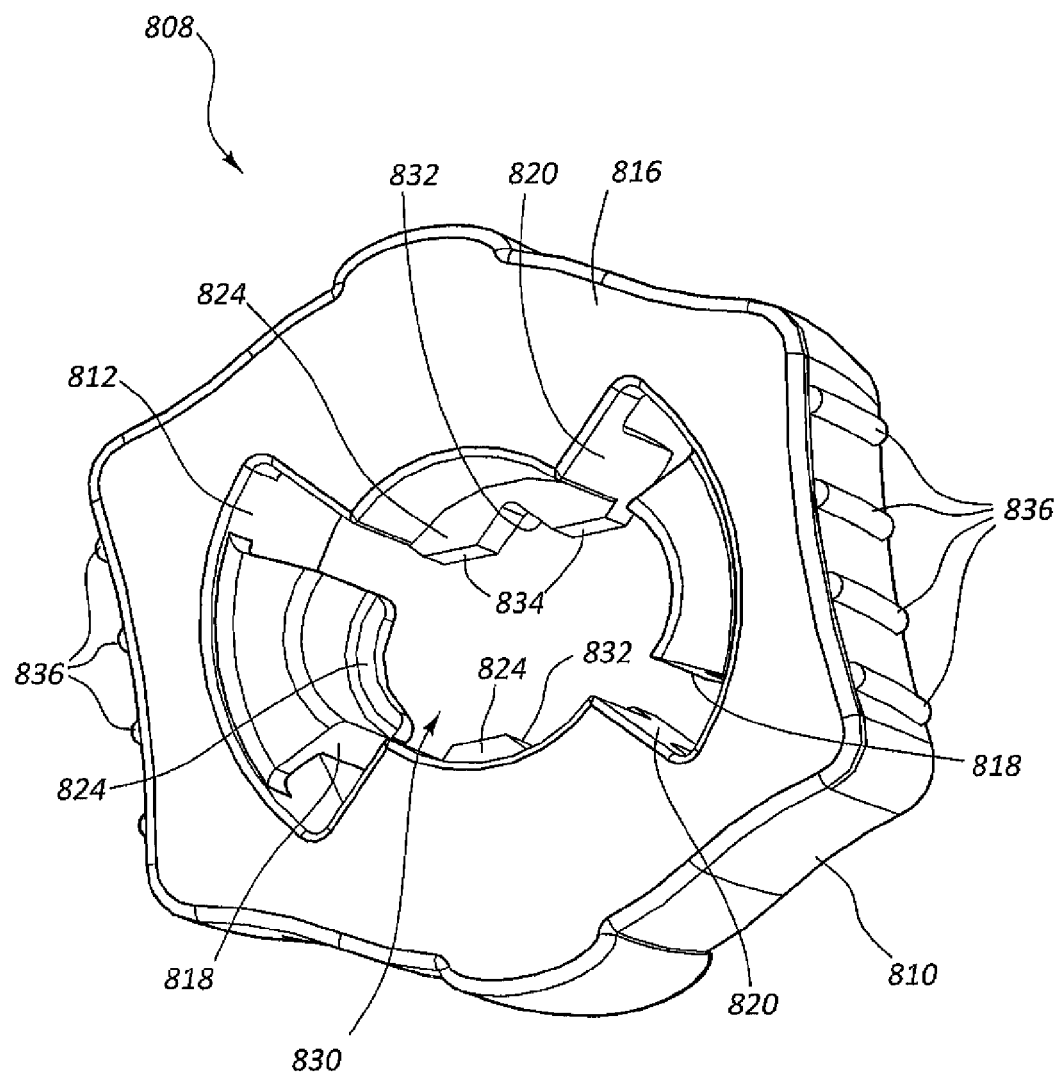

FIGS. 7A-7B show views of an embodiment of a locking member 708 according to the present disclosure. The locking member 708 may be a locking member 108 described above. The locking member 708 may comprise an outer surface 710 and inner surface 712 generally forming a ring. The outer surface 710 may be ridged to improve grip in turning the locking member 708. The locking member 708 may also comprise an external surface 714 and internal surface 716. The external surface 714 may be configured to face externally from the cervical collar (e.g., away from the main collar body 102), and the internal surface 716 may be configured to face internally (e.g., toward the main collar body 102).

A plurality of unlocked position supports 718 and locked position supports 720 are positioned within the inner surface 712. The position supports 718, 720 may be attached to the inner surface 712 near the internal surface 716 and extend toward the plane of the external surface 714 of the locking member 708. The unlocked position supports 718 may have external surfaces 726 at a first recessed level from the external surface 714, and the locked position supports 720 may have external surfaces 728 at a second recessed level from the external surface. The first recessed level may be farther from the external surface 714 (or closer to the internal surface 716) than the second recessed level.

When a height adjustment member (e.g., height adjustment member 122 or 522) is inserted through the central opening 730 of the locking member 708, the internal sides of the tabs of the height adjustment member (e.g., tabs 550) may be disposed external to the external surfaces 726 or 728 of the position supports 718 or 720. If the tabs 550 are positioned external to the unlocked position supports 718, the height adjustment member 522 may move in and out relative to the locking member 708 and a height adjustment aperture (e.g., height adjustment aperture 120). An example of this configuration is shown in FIG. 6B. If the tabs 550 are positioned external to the locked position supports 720, the height adjustment member 522 is immobilized relative to the aperture 120 and locking member 708, as shown in FIG. 6A. In the unlocked configuration, the ridges (e.g., ridges 142, 144) are allowed to slide over each other because the height adjustment member 522 can move, but in the locked configuration, the ridges 142, 144 are pressed together and relatively immobile. Thus, by turning the locking member 708 so that the tabs 550 of the height adjustment member 522 are either external to the unlocked position supports 718 or external to the locked position supports 720, the user may selectively control whether the ridges 142, 144 are unlocked or locked. The lock position of the ridges 142, 144 also controls whether the chin support member and main collar body are relatively movable around the pivotal connections 118. Thus, the position of the locking member 108, 708 may control whether height adjustment of the collar 100 is locked or unlocked, and turning the locking member 108, 708 may allow the user to change whether height adjustment of the cervical collar is allowed.

The ridges 142, 144 may be relatively movable over each other due to the internal surface 134 and external surface 140 being permitted to be drawn apart. When these surfaces 134, 140 are capable of being drawn apart, the height adjustment member 522 and height adjustment aperture 120 may be moved relative to each other. The locking member 108, 708 may also be movable relative to the height adjustment member 522 in this position. For example, if locking member 108, 708 is unlocked, the ridges 142, 144 may move relative to each other, but if they are pressed together in this position, there will be space between the locking member 108, 708 and the tabs extending from the end of the height adjustment member 522. The space may be thus present because the tabs are external to the unlocked position supports 718 in the unlocked position rather than being external to the locked position supports 720, and the unlocked position supports 718 extend externally to a shorter distance than the locked position supports 720, thereby leaving space between the tabs and the locking member 108, 708.

The external surface 714 may include an arrow or other symbol or indicator 722 adjacent to either the unlocked or locked position supports 718, 720. In some embodiments, the indicator 722 may be an arrow that points toward the indicator surface 555 of the height adjustment member 522, and the indicator surface 555 may have a symbol on it signifying whether the locking member 108, 708 is in a locked position or an unlocked position. For example, the indicator 722 may point toward a lock symbol on the indicator surface 555 when the locking member 708 is locked, but when the locking member 708 is unlocked, the indicator 722 may not be directed toward the lock symbol due to rotation of the locking member 708.

Each of the position supports 718, 720 may comprise an overhanging tab 724 radially extending inward relative to the inner surface 712 of the locking member 708 and the rest of the length of the position supports 718, 720. The height adjustment member may be inserted through central opening 730 between the position supports 718, 720. The height adjustment member may be thus inserted by being introduced to the locking member from the internal side of the locking member 708 and then pushed through the position supports 718, 720. In some embodiments, the position supports 718,720 may be at least partially flexible and may flex toward the inner surface 712 as the height adjustment member is pressed through the locking member 708. The height adjustment member may have a width (e.g., width Y in FIG. 5) at its external end that is greater than a width of a central shaft (e.g., width of shaft 548). Thus, one or more position supports 718, 720 may flex outward as the height adjustment member is pressed through them, and after being pressed through to a sufficient depth, the position supports 718, 720 may flex back into the positions shown in FIGS. 7A-7B.

Once the position supports 718, 720 move back to their rest positions, the locking member 708 may be secured to the shaft of the height adjustment member by interference of the extra width (e.g., Y) and the width of the space between the position supports 718, 720. The ease of insertion of the height adjustment member through the locking member 708 may be improved by using overhanging tabs 724 on the position supports 718, 720 since the position members 718, 720 may be thinner toward the internal surface 716 of the locking member 708 (i.e., where they need to flex to accommodate the external end of the height adjustment member) yet may be wide enough to prevent the height adjustment member from freely withdrawing from the locking member 708 due to the overhanging tabs 724 extending inward nearer to the external surfaces 726, 728 (i.e., where they need to sit to restrict withdrawal of an inserted height adjustment member). In some embodiments, there may be a space between unlocked position supports 718 that may allow the tabs 550 to at least partially withdraw between them.

The inner surface 712, unlocked position supports 718, and locked position supports 720 define the central opening 730 of the locking member 708. As shown in FIGS. 7A-7B, the opening 730 may be non-circular. Thus, the inner surface 712 may be closer to the outer surface 710 of the locking member 708 along a first lateral axis as compared to a second lateral axis of the opening 730 (e.g., a second lateral axis perpendicular to the first lateral axis). In the pictured embodiment, the inner surface 712 is closer to the outer surface 710 at the long axis of the elliptical shape of the opening 730 adjacent to the unlocked position supports 718, and the inner surface 712 is farther from the outer surface 710 at the short axis of the elliptical shape adjacent to the locked position supports 720. Thus, when a distal end of the height adjustment member 522 (e.g., the end bearing the tabs 550) may be inserted into the locking member 708, the opening 730 may only allow the height adjustment member 522 to be inserted in one relative rotated orientation. If their rotated orientation is not matched, the tabs 550 may prevent the height adjustment member 522 from entering the opening 730.

After the height adjustment member 522 is partially inserted into the opening 730 from the side of the internal surface 716 of the locking member 708, the overhanging tabs 724 may prevent further insertion due to their overhanging the opening 730 and thereby limiting the depth of insertion. The locked and unlocked position supports 718, 720 may therefore be elastically deformable or bendable at least outward toward the inner surface 712 of the locking member 708 so that the tabs 550 of the height adjustment member 522 can be snap-fit past the overhanging tabs 724 and extend to where the tabs 550 are external to the external surfaces 726, 728 of the supports 718, 720 and the shaft 548 is laterally adjacent to the overhanging tabs 724. While in FIGS. 7A-7B the opening 730 is generally elliptical, it will be apparent to those having ordinary skill in the art that have the benefit of the present disclosure that other shapes of an opening 730 may be used to perform the functions of the generally elliptical shape shown. In some embodiments, the opening 730 may be circular or another shape allowing a height adjustment member 522 to be inserted in more than one orientation.

The tabs 724 of the locked position supports 720 may comprise keyways 732. The keyways 732 may be formed in one or more overhanging tabs 724 and may correspond in size and position with key ridges 554 on a height adjustment member 522 inserted through the locking member 708. The keyways 732 may be used to prevent the height adjustment member 522 from being pressed or snap-fit past the overhanging tabs 724 unless the key ridges 554 align with and pass through the keyways 732 as the height adjustment member 522 passes the overhanging tabs 724. The keyways 732 may also be used in embodiments where the opening 730 only allows a height adjustment member 522 to be inserted in one relative orientation.

The keyways 732 may be sized and shaped to receive the key ridges 554 of the height adjustment member 522. In FIGS. 7A-7B, the keyways 732 are generally semicircular, and in FIG. 5 the key ridges 554 are generally triangular, yet the sizes and positions of the keyways 732 and key ridges 554 allow the key ridges 554 to pass through the keyways 732 when the height adjustment member 522 and locking member 708 are in the properly relatively rotated position. In some embodiments, the shape of the keyways 732 may match the shape of the key ridges 554, such as keyways having triangular cutout shape about the same size as triangular key ridges (see, e.g., keyways 832 of FIGS. 8A-8B), or circular key ridges may be provided on the height adjustment member to match the circular keyways on the overhanging tabs.

Keyways 732 and key ridges 554 may thus be used to force a specific relatively rotated orientation of the height adjustment member 522 and the locking member 708 when they are attached to each other. The keyways 732 and key ridges 554 may also force a specific orientation when a locking member 708 is removed from the height adjustment member 522. In this scenario, the locking member 708 may need to be turned around the height adjustment member 522 so that the keyways 732 and key ridges 554 align, and then the unlocked position supports 718 must be drawn outward toward the inner surface 712 to allow the tabs 550 of the height adjustment member 522 to be withdrawn through the opening 730. In at least these arrangements, the unlocked position supports 718 may be more flexible than the locked position supports 720.

In the embodiment of FIGS. 7A-7B, two unlocked position supports 718 are provided at each side of the opening 730 and one locked position support 720 is provided at each side of the opening 730. In some embodiments, the pairs of unlocked position supports 718 may be merged into a single unlocked position support (see, e.g., unlocked position supports 818 of FIGS. 8A-8B), or the locked position supports 720 may be divided into more than one support each. In this manner, the designer may use the size and number of the position supports as a means for controlling the collective rigidity or flexibility of the position supports.

FIGS. 8A-8B show another embodiment of a locking member 808 for use in locking a height adjustment member (e.g., height adjustment member 522) relative to a height adjustment aperture (e.g., height adjustment aperture 120). Similar to the locking member 708 of FIGS. 7A-7B, this locking member 808 includes outer and inner surfaces 810, 812 and external and internal surfaces 814, 816. Unlocked position supports 818 having external surfaces 826 and locked position supports 820 having external surfaces 828 are within the inner surface 812. The external surfaces 826 of the unlocked position supports 818 may extend farther from the internal surface 816 than the external surfaces 828 of the locked position supports 820. An arrow or other indicator 822 may be positioned on the external surface 814. Each of the position supports 818, 820 include overhanging tabs 824. An opening 830 may be formed by the inner surface 812 and the position supports 818, 820. The overhanging tabs 824 of the locked position supports 820 may have triangular keyways 832 shaped to receive key ridges (e.g., key ridges 554) of a height adjustment member. The tabs 824 may also comprise locking surfaces 834.

As illustrated by this embodiment, the outer surface 810 of the locking member 808 may be non-circular. In this case, the non-circular shape may be referred to as being generally hexagonal. Other shapes will be apparent to those having ordinary skill in the art and the benefit of this disclosure. Flattened surfaces of the generally hexagonal shape may improve grip of the user and give him a better sense of the degrees through which the locking member 808 has been turned while the locking member is not visible (e.g., not visible due to being under the operator's chin).

Ridges 836 may be formed on the outer surface 810 on each portion of the outer surface 810 or just on selected sides or surfaces. In FIGS. 8A-8B, the ridges 836 are only on two sides of the generally hexagonal shape. Placing the ridges 836 on the sides of the outer surface 810 that are not adjacent to the indicators 822 may suggest to the user to turn the locking member 808 around a height adjustment member by holding the outer surface 810 at those two sides, thereby limiting obstruction of the indicators 822 by the user's hand.

Similar to the locking member 708 described above, the opening 830 may receive a height adjustment member 522, but in this embodiment there are only two unlocked position supports 818. Decreasing the number of unlocked position supports 818 may increase the resistance of each unlocked position support 818 against deformation, thereby increasing the difficulty of installing or removing the locking member 808 from the height adjustment member 522.

Figure 9A:
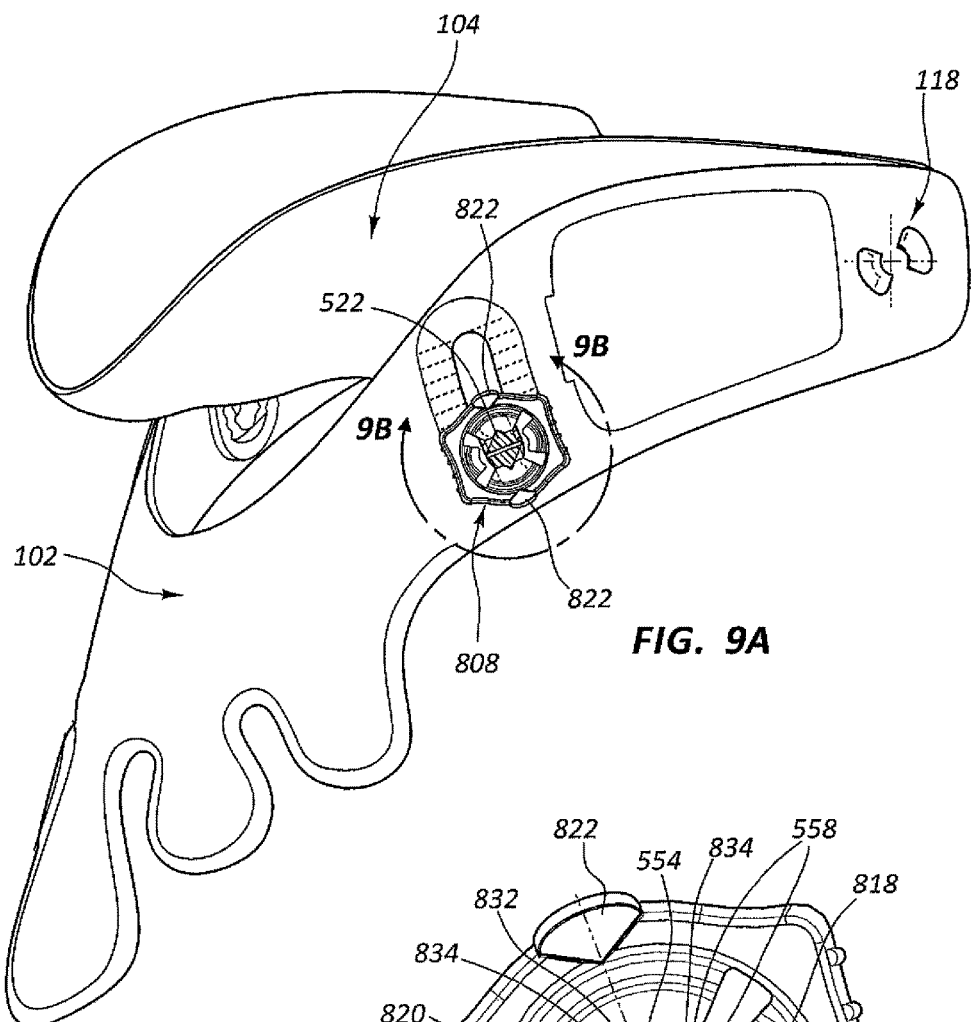
FIG. 9A is a view of a locked chin support member, main collar body, and locking member in a lowered position.
Figure 10A:
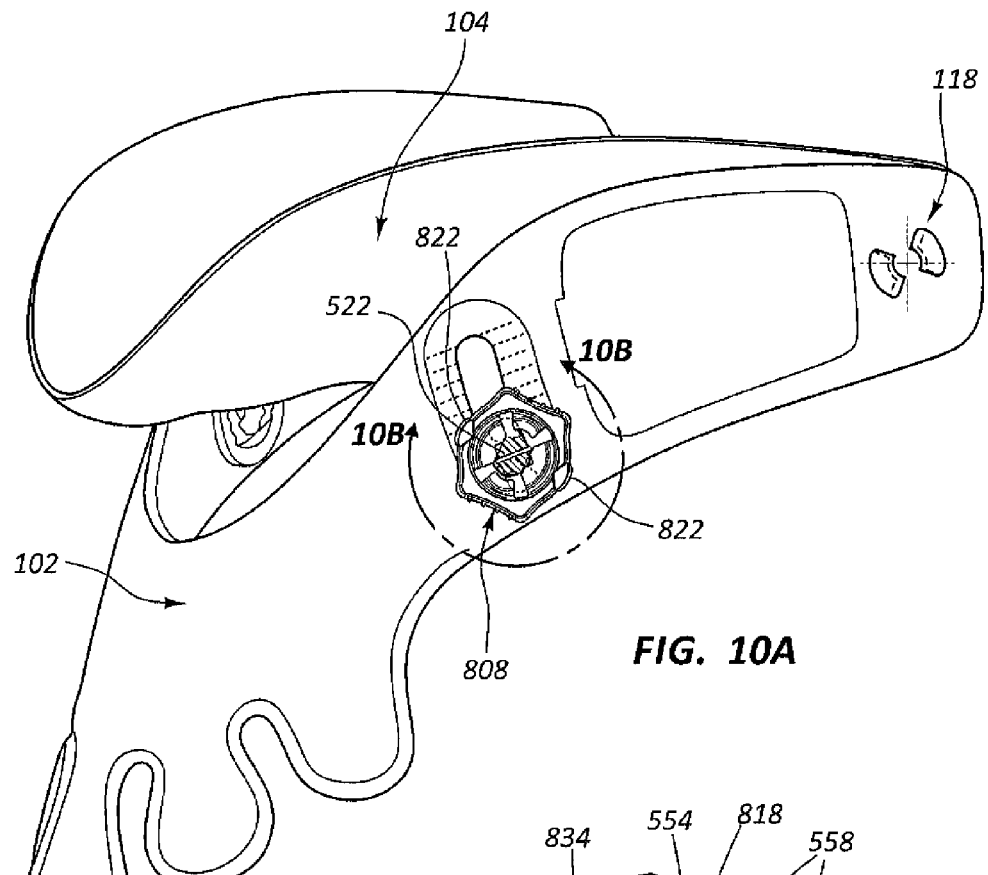
FIG. 10A is a view of a partially unlocked chin support member, main collar body, and locking member.

FIGS. 9A, 10A, 11A, and 12A show side views of a main collar body 102, chin support member 104, and locking member 808 in different relative positions. In FIG. 9A, the chin support member 104 is in a lowered position relative to the main collar body 102, and the locking member 808 is in a locked position, as indicated by the locking indicators 822 directed toward the tabs of the height adjustment member 522. In FIG. 10A, the locking member 808 is partially rotated; in FIG. 11A, the locking member 808 is rotated into an unlocked position; and in FIG. 12A, the locking member is locked again and the chin support member 104 is in a raised position relative to the main collar body 102.

FIGS. 9B, 10B, 11B, and 12B show cross-sectional views taken through the shaft 548 of the height adjustment member 522 of FIGS. 9A, 10A, 11A, and 12A and through the locked and unlocked position supports 820, 818 of the locking member 808. The cross-section is taken through the shaft 548 along the length X where the locked position supports 820 have tabs 824 adjacent to the shaft 548. As shown here, the locked position supports 820 of the locking member 808 may include locking surfaces 834 adjacent to the keyways 832 of the locked position supports 820. These locking surfaces 834 can also be seen in FIGS. 8A-8B, and corresponding locking surfaces 734 are in FIGS. 7A-7B.

Figure 9B:
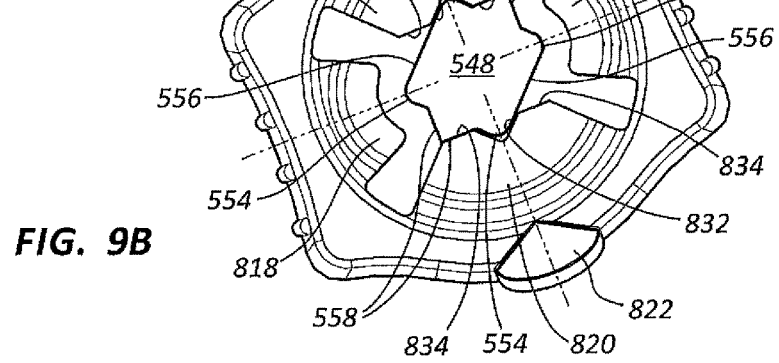
FIG. 9B is a section view of the chin support member, main collar body, and locking member of FIG. 9A taken through a plane perpendicular to the longitudinal axis of the shaft of the height adjustment member of the chin support member.

With the height adjustment member 522 inserted through the locking member 808, as shown in FIG. 9B, at least one locking surface 834 may be in contact with a restrictive surface 558 of the shaft 548 of the height adjustment member 522, and key ridges 554 on the shaft 548 may be seated in keyways 832. Another locking surface 834 of the locked position support 820 may be facing a permissive surface 556 of the shaft 548. The contact between locking surfaces 834 and restrictive surfaces 558 may prevent the locking member 808 from rotating around the shaft 548 in a direction that further drives the locking surfaces 834 and restrictive surfaces 558 into each other. The locking member 808 may, however, be rotated in a direction driving a locking surface 834 toward a permissive surface 556, as shown in FIG. 10B, where the locking member 808 has been rotated counterclockwise about 45 degrees, and in FIG. 11B, where the locking member 808 has been rotated about 90 degrees counterclockwise.

Figure 10B:
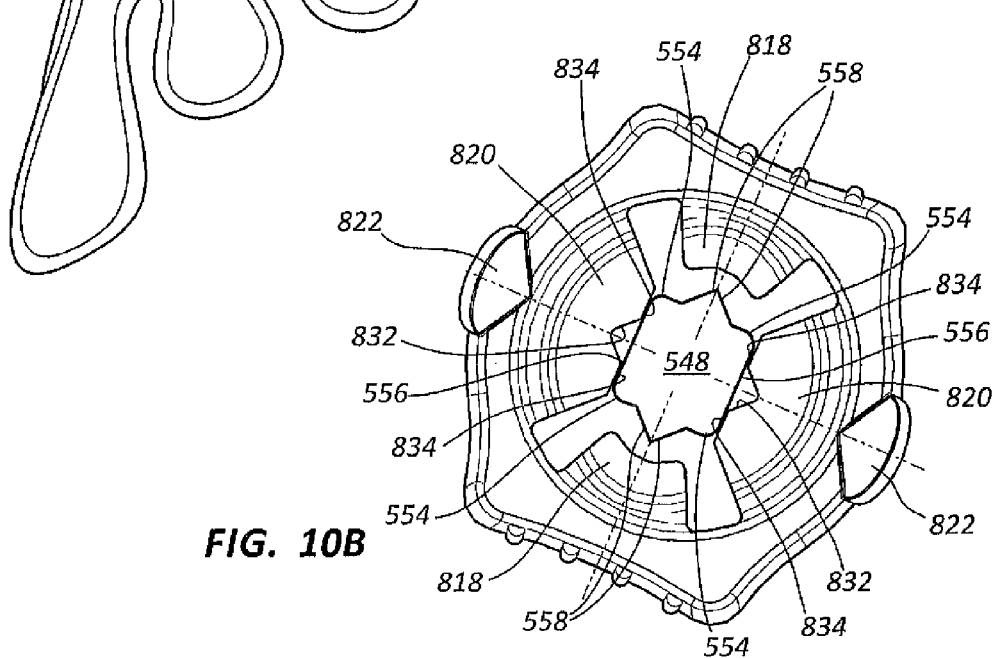
FIG. 10B is a section view of the chin support member, main collar body, and locking member of FIG. 10A taken through a plane perpendicular to the longitudinal axis of the shaft of the height adjustment member of the chin support member.
Figure 11A:
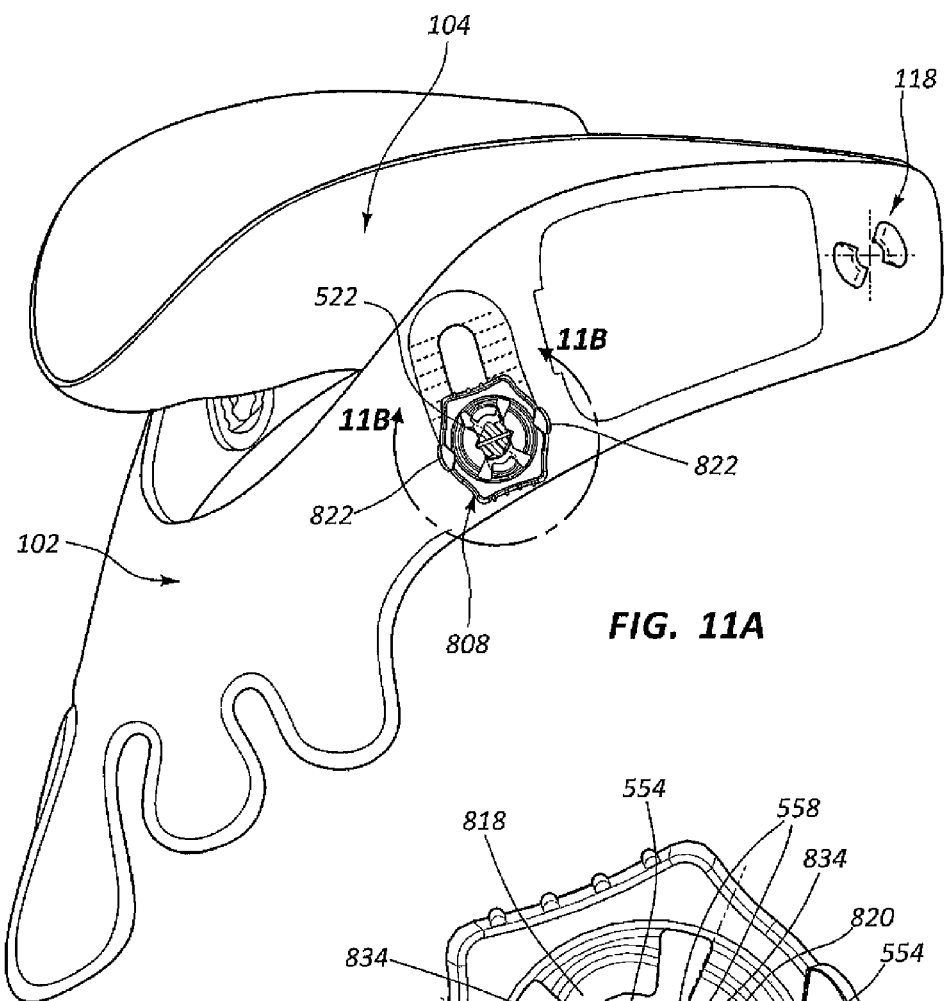
FIG. 11A is a view of a fully unlocked chin support member, main collar body, and locking member.
Figure 11B:
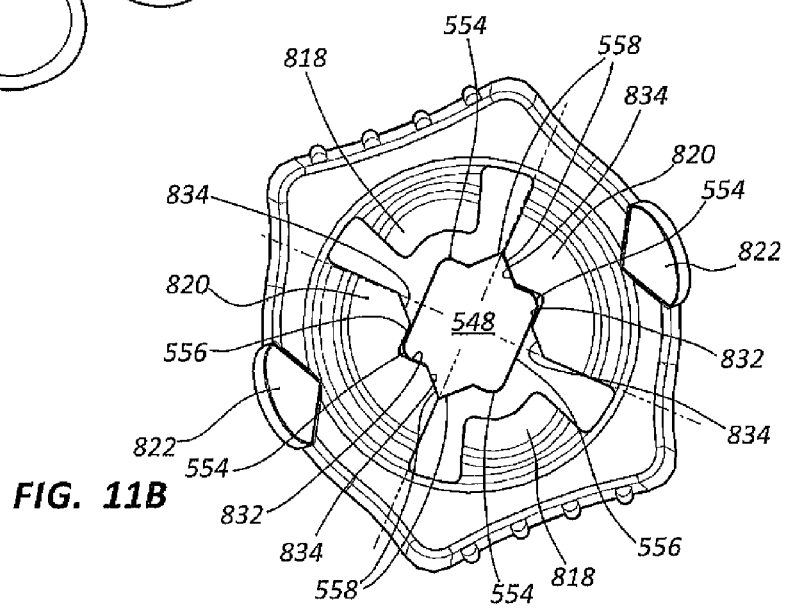
FIG. 11B is a section view of the chin support member, main collar body, and locking member of FIG. 11A taken through a plane perpendicular to the longitudinal axis of the shaft of the height adjustment member of the chin support member.

To reach the position of FIG. 10B from the position of FIG. 9B, a force may applied to the locking member 808 to rotate it around the shaft 548. In response to the rotating force, the key ridges 554 may resist movement of the locking member 808 around the shaft 548 due to their seating in the keyways 832. Thus, rotation of the locking member 808 may require outward flexure of the locked position supports 820 toward the inner surface 812 in order to allow the key ridges 554 to rotate out of the keyways 832 into the position of FIG. 10B. The materials may also be deformable to allow this rotation. When rotating between the positions of FIGS. 10B and 11B, the locked position supports 820 may again flex outward so that the key ridges 554 may be seated in the keyways 832 as shown in FIG. 11B. After rotation from the position of FIG. 9B to the position of FIG. 11B, the locking surfaces 834 formerly adjacent to restrictive surfaces 558 in FIG. 9B are now facing the permissive surfaces 556 in FIG. 11B, and the locking surfaces 834 that were facing the permissive surfaces 556 in FIG. 9B are now facing restrictive surfaces 558 in FIG. 11B.

Figure 12A:
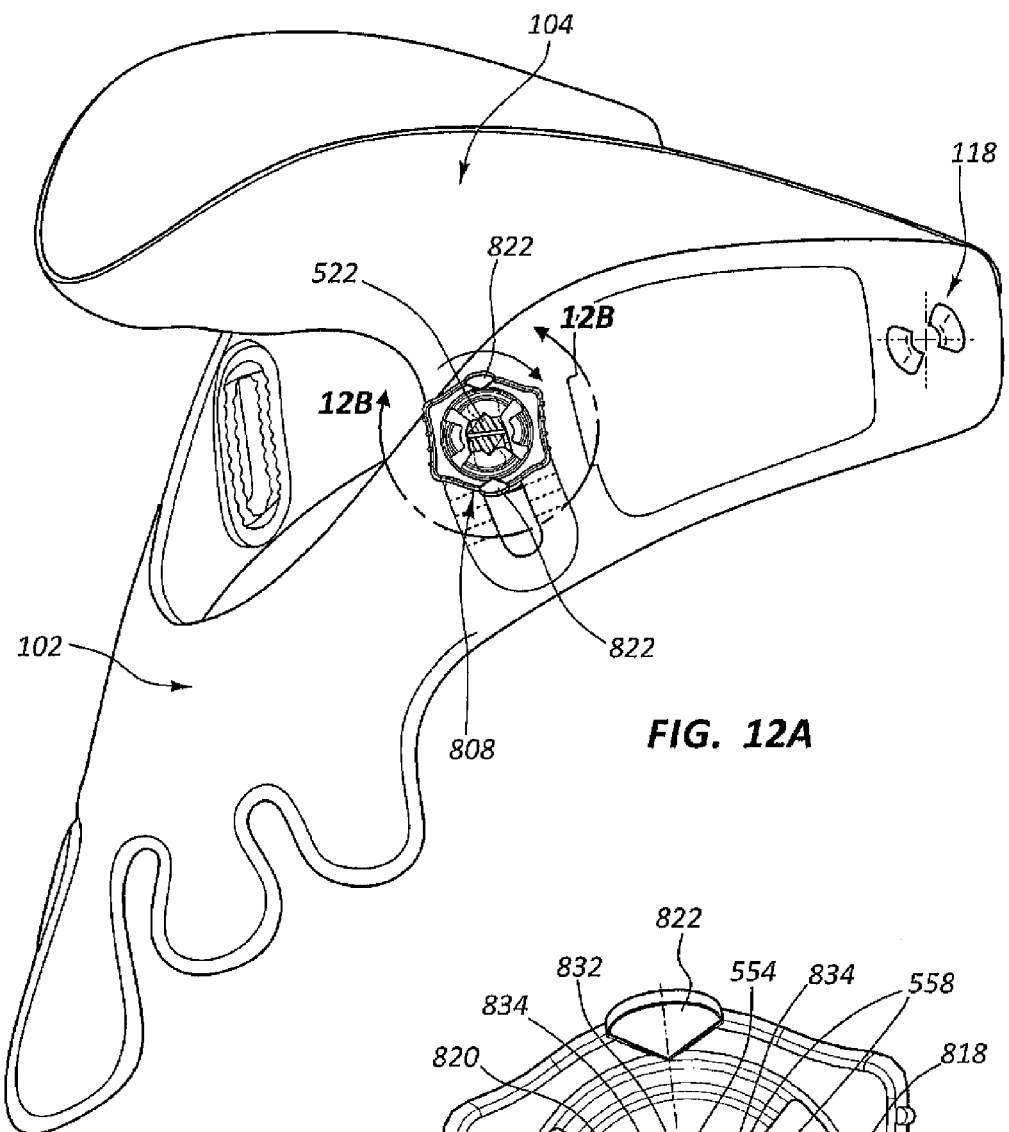
FIG. 12A is a view of a locked chin support member, main collar body, and locking member in a raised position.
Figure 12B:
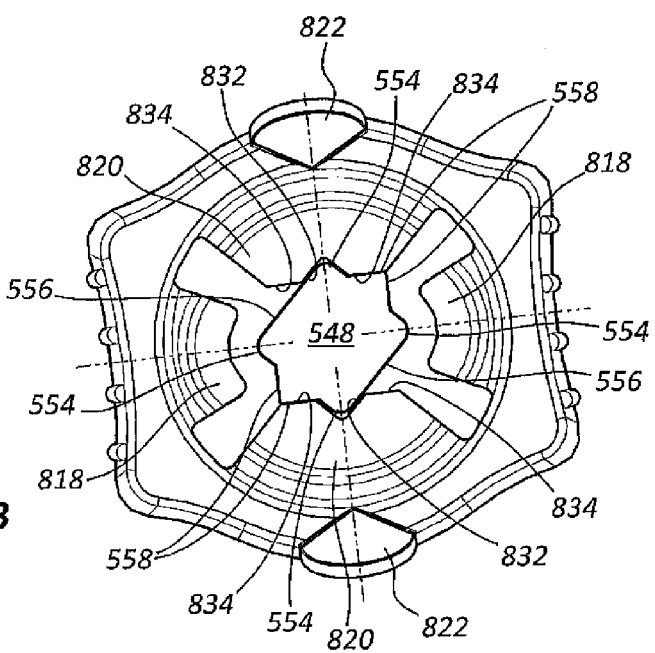
FIG. 12B is a section view of the chin support member, main collar body, and locking member of FIG. 12A taken through a plane perpendicular to the longitudinal axis of the shaft of the height adjustment member of the chin support member.

Once reaching the position of FIG. 11B, the locking member 808 may be in an unlocked position, and the chin support member 104 may be pivoted upward relative to the main collar body 102. The height adjustment member 522 may move through the height adjustment aperture, such as to the position shown in FIG. 12A. As shown in FIG. 12B, the locking member 808 may then be moved back into the locked position of FIG. 9B to keep the chin support member 104 from making any undesired movements.

The locking member 808 may be referred to as being in a "locked position" when the radially extending tabs 550 of the height adjustment member 522 are in a position external and adjacent to the locked position supports 820, and the locking member 808 may be referred to as being in an "unlocked position" when the tabs 550 are in a position external and adjacent to the unlocked position supports 818. The position of the locking member 808 may be considered locked in the locked position since the position of the tabs 550 in that position may drive the ridges of the main collar body 102 and the ridges of the chin support member 104 into each other, thereby locking or at least inhibiting relative movement of the main collar body 102 and the chin support member 104. Similarly, in the unlocked position, the ridges of the main collar body 102 and chin support member 104 are not locked or forced together, so when the chin support member 104 and main collar body 102 are relatively pivoted by the user, the ridges can move over each other.

In some embodiments, the locking member 808 may only rotate in one direction between the locked position and the unlocked position. For example, to unlock the locking member 808, it may in some cases only be rotated clockwise or counterclockwise, and the locking member 808 may stop rotating once reaching the unlocked position. It may stop rotating due to contact between a locking surface 834 and a restrictive surface 558. The locking member 808 may be rotated in the opposite direction to lock it again. In other embodiments, the locking member 808 may be rotated in one direction between the locked and unlocked positions, and if the locking member 808 continues to rotate it may be locked again. In some arrangements, the locking member 808 may move from a locked position to an unlocked position by being rotated in more than one direction, such as being unlocked no matter whether it is turned clockwise or counterclockwise.

The locking member 808 may be referred to as being in a "seated position" when the key ridges 554 of a height adjustment member 522 are seated in keyways 832 of a locking member 808. Thus, the locked position and the unlocked position of the locking member 808 may be seated positions between which the locking member 808 may be rotated.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A height-adjustable cervical collar, comprising:
   a main collar body having a collar front portion and collar side portions, the collar front portion configured to be positioned anterior to a neck and upper chest area of a wearer, the collar side portions configured to be laterally positioned relative to sides of a neck of a wearer of the height-adjustable cervical collar, at least one of the collar side portions comprising at least one height adjustment aperture;
   a chin support member coupled to the main collar body, the chin support member having a chin front portion and chin side portions configured to be at least partially positioned below a chin and lower jaw of the wearer, the chin support member comprising:
   a pair of pivotable connections coupling the chin side portions to the collar side portions;
   a height adjustment member extending externally through the height adjustment aperture of the main collar body;
   a locking member positioned around the height adjustment member external to the height adjustment aperture, the locking member being adjustable relative to the height adjustment member between a first position and a second position, wherein in the first position, pivoting movement of the chin support member relative to the main collar body around the pair of pivotable connections is permitted and in the second position, pivoting movement of the chin support member relative to the main collar body is inhibited, wherein the locking member is rotatable around the height adjustment member between the first position and the second position.

2. The height-adjustable cervical collar of claim 1, wherein the locking member is rotatable from the first position to the second position in only one direction of rotation.

3. A height-adjustable cervical collar, comprising:
a main collar body having a collar front portion and collar side portions, the collar front portion configured to be positioned anterior to a neck and upper chest area of a wearer, the collar side portions configured to be laterally positioned relative to sides of a neck of a wearer of the height-adjustable cervical collar, at least one of the collar side portions comprising at least one height adjustment aperture;
a chin support member coupled to the main collar body, the chin support member having a chin front portion and chin side portions configured to be at least partially positioned below a chin and lower jaw of the wearer, the chin support member comprising:
 a pair of pivotable connections coupling the chin side portions to the collar side portions;
 a height adjustment member extending externally through the height adjustment aperture of the main collar body;
a locking member positioned around the height adjustment member external to the height adjustment aperture, the locking member being adjustable relative to the height adjustment member between a first position and a second position, wherein in the first position, pivoting movement of the chin support member relative to the main collar body around the pair of pivotable connections is permitted and in the second position, pivoting movement of the chin support member relative to the main collar body is inhibited;
wherein the height adjustment member further comprises a tab extending radially from the height adjustment member;
wherein the tab is spaced from the locking member when the locking member is in the first position and the tab is in contact with the locking member when the locking member is in the second position.

4. The height-adjustable cervical collar of claim 3, wherein the locking member comprises a first surface and a second surface, each of the first and second surfaces being selectively rotatable into alignment with the tab, the second surface being externally raised relative to the first surface.

5. The height-adjustable cervical collar of claim 3, wherein the tab is inwardly compressible toward a central axis of the height adjustment member.

6. A height-adjustable cervical collar, comprising:
a main collar body having a collar front portion and collar side portions, the collar front portion configured to be positioned anterior to a neck and upper chest area of a wearer, the collar side portions configured to be laterally positioned relative to sides of a neck of a wearer of the height-adjustable cervical collar, at least one of the collar side portions comprising at least one height adjustment aperture;
a chin support member coupled to the main collar body, the chin support member having a chin front portion and chin side portions configured to be at least partially positioned below a chin and lower jaw of the wearer, the chin support member comprising:
 a pair of pivotable connections coupling the chin side portions to the collar side portions;
 a height adjustment member extending externally through the height adjustment aperture of the main collar body;
a locking member positioned around the height adjustment member external to the height adjustment aperture, the locking member being adjustable relative to the height adjustment member between a first position and a second position, wherein in the first position, pivoting movement of the chin support member relative to the main collar body around the pair of pivotable connections is permitted and in the second position, pivoting movement of the chin support member relative to the main collar body is inhibited;
wherein the main collar body further comprises a first ridged surface and the chin support member further comprises a second ridged surface;
wherein when the locking member is in the first position, the first and second ridged surfaces are relatively slidable over each other, and when the locking member is in the second position, the first and second ridged surfaces are not relatively slidable.

7. The height-adjustable cervical collar of claim 6, wherein the wherein the first and second ridged surfaces are relatively slidable over each other between a plurality of adjusted positions.

8. The height-adjustable cervical collar of claim 6, wherein the pair of pivotable connections removably secure the main collar body and chin support member together and wherein the chin support member and main collar body are separable from each other upon relative rotation to a predetermined position.

9. A method of manufacturing a height-adjustable cervical collar, the method comprising:
providing a pivotal connection between a chin support member and a main collar body of a cervical collar;
inserting a height adjustment member of the chin support member through a height adjustment aperture in the main collar body;
positioning a locking member around the height adjustment member such that the locking member is movable along a length of the height adjustment member between a first position in which the chin support member and cervical collar are adjustable relative to each other and a second position in which the chin support member and cervical collar are fixed relative to each other;
wherein the locking member is positioned around the height adjustment member in a manner permitting rotation of the locking member around the height adjustment member.

10. The method of claim 9, further comprising:
pivoting the pivotal connection while the locking member is in the first position;
inhibiting rotation of the pivotal connection while the locking member is in the second position, wherein rotation is inhibited by ridges on the chin support member and the main collar body being pressed into an interlocking position interfering with rotation at the pivotal connection.

11. A cervical collar, comprising:
a lower support member configured to at least partially overlie the upper chest of a wearer, the lower support member having a first ridged surface;

an upper support member pivotally connected to the lower support member, the upper support member having a second ridged surface, the second ridged surface facing the first ridged surface;

a releasable tensioning member connected to the cervical collar, the tensioning member having an unlocked position and a locked position, the unlocked position allowing relative movement of the first and second ridged surfaces, the locked position preventing relative movement of the first and second ridged surfaces by applying tension driving the first and second ridged surfaces into contact;

wherein the tensioning member is rotatable between the locked and unlocked positions.

12. The cervical collar of claim 11, wherein the first ridged surface is positioned on a first surface and the second ridged surface is positioned on a second surface, the first and second surfaces being arranged in parallel with each other.

13. The cervical collar of claim 12, wherein the first and second surfaces are planar surfaces.

* * * * *